United States Patent
Xie et al.

(10) Patent No.: US 9,340,492 B2
(45) Date of Patent: May 17, 2016

(54) META-DIARYLANILINE OR META-DIARYLPYRIDINAMINE COMPOUND, PREPARATION METHOD AND MEDICAL USES THEREOF

(71) Applicant: INSTITUTE OF PHARMACOLOGY AND TOXICOLOGY ACADEMY OF MILITARY MEDICAL SCIENCES P.L.A. CHINA, Beijing (CN)

(72) Inventors: Lan Xie, Beijing (CN); Chin-Ho Chen, Chapel Hill, NC (US); Lianqi Sun, Beijing (CN); Na Liu, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 14/415,846

(22) PCT Filed: Jul. 15, 2013

(86) PCT No.: PCT/CN2013/079345
§ 371 (c)(1),
(2) Date: Jan. 20, 2015

(87) PCT Pub. No.: WO2014/012467
PCT Pub. Date: Jan. 23, 2014

(65) Prior Publication Data
US 2015/0218088 A1    Aug. 6, 2015

(30) Foreign Application Priority Data
Jul. 20, 2012 (CN) .......................... 2012 1 0252514

(51) Int. Cl.
| | | |
|---|---|---|
| *C07D 213/70* | (2006.01) | |
| *C07C 255/34* | (2006.01) | |
| *C07D 213/74* | (2006.01) | |
| *C07C 311/39* | (2006.01) | |
| *C07C 255/58* | (2006.01) | |
| *C07C 253/14* | (2006.01) | |
| *C07C 253/30* | (2006.01) | |
| *C07C 255/33* | (2006.01) | |
| *C07C 255/64* | (2006.01) | |
| *C07D 213/75* | (2006.01) | |
| *C07D 213/76* | (2006.01) | |

(52) U.S. Cl.
CPC ............. *C07C 255/34* (2013.01); *C07C 253/14* (2013.01); *C07C 253/30* (2013.01); *C07C 255/33* (2013.01); *C07C 255/58* (2013.01); *C07C 255/64* (2013.01); *C07C 311/39* (2013.01); *C07D 213/74* (2013.01); *C07D 213/75* (2013.01); *C07D 213/76* (2013.01); *C07C 2101/02* (2013.01)

(58) Field of Classification Search
None
See application file for complete search history.

(56) References Cited

U.S. PATENT DOCUMENTS

| | | | |
|---|---|---|---|
| 8,933,106 B2 * | 1/2015 | Xie et al. | ....................... 514/352 |
| 2012/0053213 A1 | 3/2012 | Xie et al. | |

FOREIGN PATENT DOCUMENTS

CN          101717364 A          6/2010

OTHER PUBLICATIONS

Tian, X. et al., Bioorg Med Chem Lett 2009 vol. 19, pp. 5482-5485.*
International Search Report mailed Oct. 24, 2013 (PCT/CN2013/079345); ISA/CN.
Sun, Lianqi et al. Design, Synthesis, and Preclinical Evaluations of Novel 4-Substituted 1, 5-Diarylanilines as Potent HIV-1 Non-nucleoside Reverse Transcriptase Inhibitor (NNRTI) Drug Candidates. Journal of Medicinal Chemistry, Aug. 2, 2012, vol. 55, No. 16, pp. 7219-7229, including supporting information.
Sun, Lianqi et al. New HIV-NNRTIs Lead Diarylanilines: Optimization and Evaluation of Drug-like Properties. China Master's Theses Full-text Database, Medicine and Health Sciences, Jul. 15, 2012, No. 7, E079-22, English Abstract, pp. 13-15.
Sun, Lianqi et al. Optimization of 2, 4-Diarylanilines as Non-nucleoside HIV-1 Reverse Transcriptase Inhibitors. Bioorganic & Medicinal Chemistry Letters, Feb. 24, 2012, vol. 22, No. 7, pp. 2376-2379.
Tian, Xingtao et al. Design, Synthesis, and Evaluation of Diarylpyridines and Diarylanilines as Potent Non-nucleoside HIV-1 Reverse Transcriptase Inhibitors. Journal of Medicinal Chemistry, Apr. 11, 2010, vol. 53, No. 23, pp. 8287-8297, including supporting information.

* cited by examiner

Primary Examiner — Heidi Reese
(74) Attorney, Agent, or Firm — Banner & Witcoff, Ltd.

(57) ABSTRACT

Meta-diarylaniline or meta-diarylpyridinamine compounds, methods for preparing the same and uses thereof in manufacture of a medicament. The compounds according to the present application have strong inhibitory activity (at nM level) against wild-type and various drug-resistant HIV viral strains, exhibit good druggability, and can be easily synthesized.

13 Claims, No Drawings

META-DIARYLANILINE OR META-DIARYLPYRIDINAMINE COMPOUND, PREPARATION METHOD AND MEDICAL USES THEREOF

CROSS-REFERENCE TO RELATED APPLICATIONS

The present application is a U.S. National Phase of International Application No. PCT/CN2013/079345, filed on Jul. 15, 2013, designating the United States of America and claiming priority to Chinese Patent Application No. 201210252514.7, filed Jul. 20, 2012. The present Application claims priority to and the benefit of the above-identified applications, each of which is incorporated by reference herein in its entirety.

FIELD OF THE INVENTION

The invention, which belongs to pharmaceutical and chemical engineering field, relates to meta-diarylaniline or meta-diarylpyridinamine compounds, methods for preparing the same and medical uses thereof. In particular, the invention relates to meta-diarylanilines (DAANs) and meta-diarylpyridinamines (DAPAs) compounds having anti-HIV activity, methods for preparing the same, pharmaceutical compositions comprising the same, and uses thereof in manufacture of anti-HIV drugs.

BACKGROUND OF THE INVENTION

Acquired Immune Deficiency Syndrome (AIDS) is a globally popular lethal infectious disease caused by Human Immunodeficiency Virus (HIV). HIV is a RNA virus, which destroys the immune system in human by infecting immunocytes in human and leads to complete loss of immune function in human, so that patients die of diseases caused by a variety of infections. Based on different drug targets involved in the replication of HIV virus, almost 30 anti-HIV drugs have been developed successfully by far. Said drugs can be divided into 5 classes depending on mechanism of action, i.e. Nucleoside Reverse Transcriptase Inhibitors (NRTIs), Non-Nucleoside Reverse Transcriptase Inhibitors (NNRTIs), Protease Inhibitors (PIs), fusion inhibitors (Enfuvirtide) and entry inhibitors (Maraviroc). There are already 5 commercially available NNRTIs, which use HIV reverse transcriptase as target, i.e. Nevirapine, Delavirdine, Efavirenz, Entravine (TMC125), and Rilpivirine (TMC278). Drugs of this class is non-competitive inhibitors, has superiority with respect to high efficiency, low toxicity and good synergistic effect with other classes of anti-HIV drugs, and play an important role in anti-HIV combination therapy (HAART). Since variation constantly occurs in HIV virus due to action of drugs, new drug-resistant viral strains appear continuously, which is the main problem of anti-HIV drugs. Therefore, it is very necessary and extremely urgent to look for and develop novel anti-HIV drugs having strong inhibitory activity against drug-resistant viruses.

DESCRIPTION OF THE INVENTION

The inventors further modify the structures of two anti-HIV lead compounds (i.e. meta-diarylanilines (DAANs) and meta-diarylpyridinamines (DAPDs)) to obtain novel compounds having strong inhibitory activity (at nM level) against wild-type and various drug-resistant HIV viral strains (see Tables 2 and 3 for a part of data) through deep study and creative work. Moreover, the novel active compounds also exhibit good druggability (see Table 3 for a part of data). The novel compounds according to the invention have high efficiency, low toxicity, good water solubility, log P value (<5), and metabolic stability ($t_{1/2}$), which facilitate absorption and efficacy of the drugs in vivo. The compounds according to the invention have the potential to be anti-HIV drugs. Thus, the following invention is provided.

In one aspect, the invention relates to a compound of formula (I) or a pharmaceutically acceptable salt thereof,

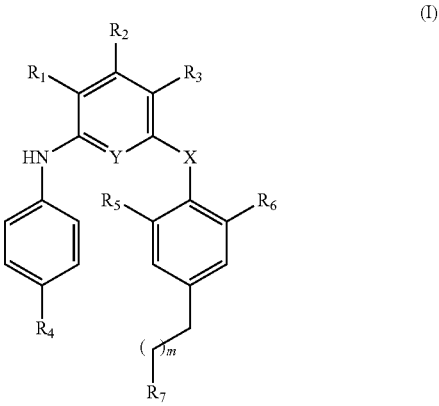

(I)

wherein $R_1$ is —$NH_2$, —OH, halogen (such as fluoroine, chlorine, bromine or iodine), —$NO_2$, —CN, —COOH, —$SO_3H$, —$OCH_3$, —$CH_3$ or —$CF_3$;

$R_2$ is H;

$R_3$ is H, OH, halogen (such as fluoroine, chlorine, bromine or iodine), —$NH_2$, cyano, triazo, ethynyl, —$NO_2$, —COOH, —$SO_3H$, —$CF_3$, vinyl, $C_{1-4}$ acyl, $C_{1-4}$ ester group, trifluoroacetoxyl, $C_{1-4}$ acyloxy, $OCONH_2$, $OCONHCH_3$, uramido, guanido, $C_{1-6}$ alkyl, $C_{1-6}$ hydroxyalkyl, $C_{1-6}$ haloalkyl, $C_{1-6}$ aminoalkyl, $C_{1-6}$ ether alkyl, $C_{1-6}$ alkoxy, $C_{1-6}$ hydroxyalkoxy, $C_{1-6}$ haloalkoxy, $C_{1-6}$ aminoalkoxy, $C_{1-6}$ ether alkoxy, $C_{1-6}$ alkylamino, $C_{1-6}$ dialkylamino, $C_{1-6}$ ether alkylamino, $C_{3-8}$ cycloalkyl, $C_{3-8}$ cyclylalkoxy, $C_{3-8}$ cyclylalkylamino, heterocyclyl (such as piperidyl, piperazinyl, morpholinyl or epoxyalkyl), 3- to 8-membered heterocyclyl substituted with $C_{1-4}$ hydroxyalkyl or $C_{1-4}$ haloalkyl or $C_{1-4}$ aminoalkyl or $C_{1-4}$ cyanoalkyl or $C_{1-4}$ ether alkyl, 3- to 8-membered heterocyclylalkyl substituted with $C_{1-4}$ hydroxyalkyl or $C_{1-4}$ haloalkyl or $C_{1-4}$ aminoalkyl or $C_{1-4}$ cyanoalkyl or $C_{1-4}$ ether alkyl, 3- to 8-membered heterocyclylalkoxy substituted with $C_{1-4}$ hydroxyalkyl or $C_{1-4}$ haloalkyl or $C_{1-4}$ aminoalkyl or $C_{1-4}$ cyanoalkyl or $C_{1-4}$ ether alkyl, or 3- to 8-membered heterocyclylalkylamino substituted with $C_{1-4}$ hydroxyalkyl or $C_{1-4}$ haloalkyl or $C_{1-4}$ aminoalkyl or $C_{1-4}$ cyanoalkyl or $C_{1-4}$ ether alkyl;

$R_4$ is —CN, —$NH_2$, —OH, halogen (such as fluoroine, chlorine, bromine or iodine), —$NO_2$, —COOH, —$SO_3H$, —$OCH_3$, —$CH_3$, —$CF_3$, vinyl, ethynyl, triazo, cyanovinyl or cyanoethynyl;

$R_5$ is $C_{1-6}$ alkyl, $C_{1-6}$ alkoxy, halogen (such as fluoroine, chlorine, bromine or iodine) or $C_{1-6}$ haloalkyl;

$R_6$ is $C_{1-6}$ alkyl, $C_{1-6}$ alkoxy, halogen (such as fluoroine, chlorine, bromine or iodine) or $C_{1-6}$ haloalkyl;

$R_6$ and $R_5$ are identical or different;

$R_7$ is —$NH_2$, —OH, halogen (such as fluoroine, chlorine, bromine or iodine), —$NO_2$, —CN, —COOH, —$SO_3H$, —$OCH_3$, —$CH_3$, —CH=CH—CN, or —$CF_3$; or $R_7$ is —NH₂, —OH, halogen (such as fluoroine, chlorine, bromine or iodine), —NO₂, —CN, —OCH₃, —CH₃, —CH=CH—CN, or —CF₃, which is linked to 1, 2, 3 or 4 —CH₂—; or R₇ is $C_{1-6}$ aminoalkyl, $C_{1-6}$ hydroxyalkyl, $C_{1-6}$ haloalkyl, $C_{1-6}$ cyanoalkyl, $C_{1-6}$ alkoxy, $C_{1-6}$ alkyl, $C_{1-6}$ alkylamino, $C_{1-6}$ dialkylamino, $C_{1-6}$ ether alkoxy, $C_{2-6}$ alkenyl or alkynyl, ene-ene-containing conjugated or non-conjugated $C_{2-6}$ hydrocarbonyl, ene-yne-containing conjugated or non-conjugated $C_{2-6}$ hydrocarbonyl, ene-carbonyl-containing conjugated or non-conjugated $C_{2-6}$ hydrocarbonyl, yne-carbonyl-containing conjugated or non-conjugated $C_{2-6}$ hydrocarbonyl, $C_{1-6}$ hydrocarbonyl substituted with one or more hydroxyl or halogen;

X is —NH— or —O—;
Y is —CH— or —N—;
m is 0, 1, 2, 3 or 4.

In another aspect, the invention relates to a compound of formula (II) or a pharmaceutically acceptable salt thereof,

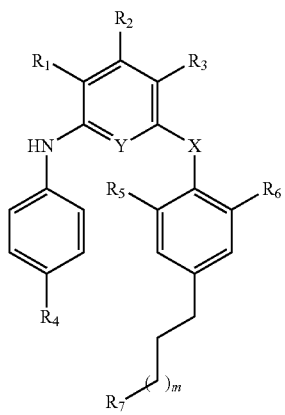

(II)

wherein
R₁ is —NH₂, —OH, halogen (such as fluoroine, chlorine, bromine or iodine), —NO₂, —CN, —COOH, —SO₃H, —OCH₃, —CH₃ or —CF₃;
R₂ is H;
R₃ is H, OH, halogen (such as fluoroine, chlorine, bromine or iodine), —NH₂, cyano, triazo, ethynyl, —NO₂, —COOH, —SO₃H, —CF₃, vinyl, $C_{1-4}$ acyl, $C_{1-4}$ ester group, trifluoroacetoxyl, $C_{1-4}$ acyloxy, OCONH₂, OCONHCH₃, uramido, guanido, $C_{1-6}$ alkyl, $C_{1-6}$ hydroxyalkyl, $C_{1-6}$ haloalkyl, $C_{1-6}$ aminoalkyl, $C_{1-6}$ ether alkyl, $C_{1-6}$ alkoxy, $C_{1-6}$ hydroxyalkoxy, $C_{1-6}$ haloalkoxy, $C_{1-6}$ aminoalkoxy, $C_{1-6}$ ether alkoxy, $C_{1-6}$ alkylamino, $C_{1-6}$ dialkylamino, $C_{1-6}$ ether alkylamino, $C_{3-8}$ cycloalkyl, $C_{3-8}$ cyclylalkoxy, $C_{3-8}$ cyclylalkylamino, heterocyclyl (such as piperidyl, piperazinyl, morpholinyl or epoxyalkyl), 3- to 8-membered heterocyclyl substituted with $C_{1-4}$ hydroxyalkyl or $C_{1-4}$ haloalkyl or $C_{1-4}$ aminoalkyl or $C_{1-4}$ cyanoalkyl or $C_{1-4}$ ether alkyl, 3- to 8-membered heterocyclylalkyl substituted with $C_{1-4}$ hydroxyalkyl or $C_{1-4}$ haloalkyl or $C_{1-4}$ aminoalkyl or $C_{1-4}$ cyanoalkyl or $C_{1-4}$ ether alkyl, 3- to 8-membered heterocyclylalkoxy substituted with $C_{1-4}$ hydroxyalkyl or $C_{1-4}$ haloalkyl or $C_{1-4}$ aminoalkyl or $C_{1-4}$ cyanoalkyl or $C_{1-4}$ ether alkyl, or 3- to 8-membered heterocyclylalkylamino substituted with $C_{1-4}$ hydroxyalkyl or $C_{1-4}$ haloalkyl or $C_{1-4}$ aminoalkyl or $C_{1-4}$ cyanoalkyl or $C_{1-4}$ ether alkyl;
R₄ is H, —CN, —NH₂, —OH, halogen (such as fluoroine, chlorine, bromine or iodine), —NO₂, —COOH, —SO₃H, —OCH₃, —CH₃, —CF₃, vinyl, ethynyl, triazo, cyanovinyl or cyano ethynyl;
R₅ and R₆ each are independently $C_{1-6}$ alkyl, $C_{1-6}$ alkoxy; halogen (such as fluoroine, chlorine, bromine or iodine) or $C_{1-6}$ haloalkyl;
R₆ and R₅ are identical or different;
R₇ is —NH₂, —OH, halogen (such as fluoroine, chlorine, bromine or iodine), —NO₂, —CN, —COOH, —SO₃H, —OCH₃, —CH₃, —CH=CH—CN, or —CF₃; or R₇ is —NH₂, —OH, halogen (such as fluoroine, chlorine, bromine or iodine), —NO₂, —CN, —OCH₃, —CH₃, —CH=CH—CN, or —CF₃, which is linked with 1, 2, 3 or 4 —CH₂—; or R₇ is $C_{1-6}$ aminoalkyl, $C_{1-6}$ hydroxyalkyl, $C_{1-6}$ haloalkyl, $C_{1-6}$ cyanoalkyl, $C_{1-6}$ alkoxy, $C_{1-6}$ alkyl, $C_{1-6}$ alkylamino, $C_{1-6}$ dialkylamino, $C_{1-6}$ ether alkoxy, $C_{2-6}$ alkenyl or alkynyl, ene-ene-containing conjugated or non-conjugated $C_{2-6}$ hydrocarbonyl, ene-yne-containing conjugated or non-conjugated $C_{2-6}$ hydrocarbonyl, ene-carbonyl-containing conjugated or non-conjugated $C_{2-6}$ hydrocarbonyl, yne-carbonyl-containing conjugated or non-conjugated $C_{2-6}$ hydrocarbonyl, $C_{1-6}$ hydrocarbonyl substituted with one or more hydroxyl or halogen;

m is 0, 1, 2 or 3;
X is —NH— or —O—;
Y is —CH— or —N—.

The compound or pharmaceutical salt thereof according to any item of the invention, wherein
R₁ is —NH₂, —OH, —F, —Cl, —Br, —I, —NO₂, —CN, —COOH, —SO₃H, —OCH₃, —CH₃ or —CF₃;
R₂ is H;
R₃ is —CF₃, —CCl₃, —CBr₃, —NO₂, —COOCH₃, —COOCH₂CH₃, —COOCH₂CH₂CH₃, —COOH, —CONH₂, —CONHCH₃, —SO₂NH₂, H, —NH₂, —CONHNH₂, —OH, —F, —Cl, —Br, —I, —NO₂, —CN, —SO₃H, —OCH₃, —CH₃, —CH₂OH, —CH₂OR', —CH₂NH₂, or —CH₂NHR'; wherein R' is

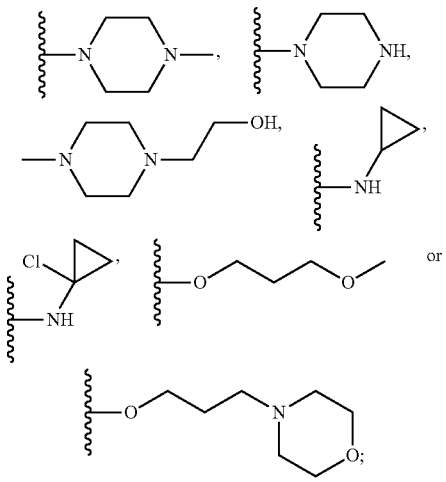

R₄ is —CN, —NH₂, —OH, —F, —Cl, —Br, —I, —NO₂, —COOH, —SO₃H, —OCH₃, —CH₃ or —CF₃;
R₅ is methyl, ethyl, n-propyl, isopropyl, methoxy, ethoxy, n-propoxy, isopropoxy, fluoro, chloro, bromo, or iodo;
R₆ is methyl, ethyl, n-propyl, isopropyl, methoxy, ethoxy, n-propoxy, isopropoxy, fluoro, chloro, bromo, or iodo;
R₆ and R₅ are identical or different;
R₇ is —(CH₂)₂—CN, —(CH₂)₂—CH₃, —(CH₂)₂—COOCH₃, —(CH₂)₃—OH,

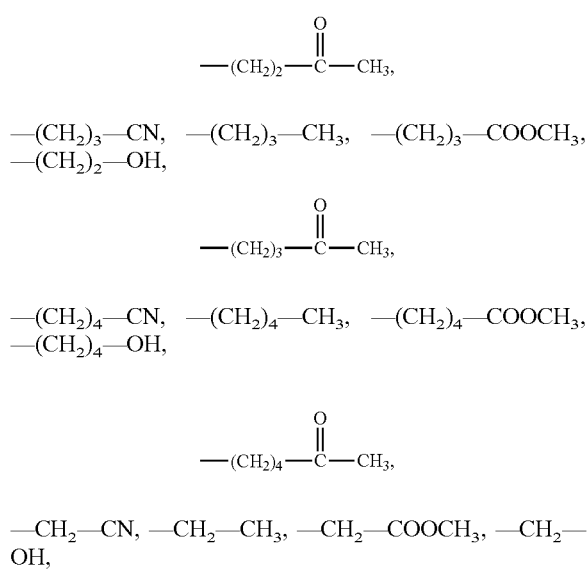

—(CH$_2$)$_3$—CN, —(CH$_2$)$_3$—CH$_3$, —(CH$_2$)$_3$—COOCH$_3$, —(CH$_2$)$_2$—OH,

—(CH$_2$)$_4$—CN, —(CH$_2$)$_4$—CH$_3$, —(CH$_2$)$_4$—COOCH$_3$, —(CH$_2$)$_4$—OH,

—CH$_2$—CN, —CH$_2$—CH$_3$, —CH$_2$—COOCH$_3$, —CH$_2$—OH, or —CH$_2$OR''; wherein R'' represents C$_{1-6}$alkyl;
X is —NH— or —O—;
Y is —CH— or —N—;

the other symbols are defined as they are in any of the preceding items.

The compound or pharmaceutical salt thereof according to any item of the invention, wherein
R$_1$ is —NH$_2$;
R$_2$ is H;
R$_3$ is —CF$_3$, —COOCH$_3$, —COOH, —CONH$_2$, —CONHCH$_3$, —SO$_2$NH$_2$, H, —NH$_2$, —CONHNH$_2$; —OH, —F, —Cl, —Br, —I, —NO$_2$, —CN, —SO$_3$H, —OCH$_3$, —CH$_3$, —CH$_2$OH, —CH$_2$OR', —CH$_2$NH$_2$, —CH$_2$NHR', —CH$_2$Cl or —CH$_2$Br;
R$_4$ is —CN;
R$_5$ is methyl, methoxy, fluoro, chloro, or bromo;
R$_6$ is methyl, methoxy, fluoro, chloro, or bromo;
R$_6$ and R$_5$ are identical or different;
R$_7$ is —(CH$_2$)$_2$—CN, —(CH$_2$)$_2$—CH$_3$, —(CH$_2$)$_2$—COOCH$_3$, —(CH$_2$)$_3$—OH or —(CH$_2$)$_2$ $$-(CH_2)_2-\underset{\underset{O}{\|}}{C}-CH_3;$$

X is —O—;
Y is —CH— or —N—;
the other symbols are defined as they are in any of the preceding items.

The compound or pharmaceutical salt thereof according to any item of the invention, selected from the compounds in Table 1 or pharmaceutically acceptable salts thereof:

TABLE 1

Some compounds of the invention

| Compound No. | Name | Structure |
|---|---|---|
| 2 | 5-(4''-cyanoethyl-2'', 6''-dimethylphenoxy)-N$^1$-(4'-cyanophenyl)-4-trifluoromethyl-1,2-phenylenediamine | 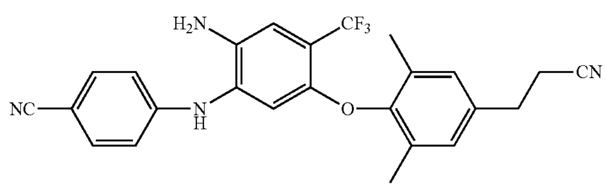 [SMILES: Cc1cc(CCC#N)cc(C)c1Oc1cc(Nc2ccc(C#N)cc2)c(N)cc1C(F)(F)F] |
| 4 | 5-(4''-cyanoethyl-2'', 6''-dimethylphenoxy)-N$^1$-(4'-cyanophenyl)-4-methoxycarbonyl-1,2-phenylenediamine | 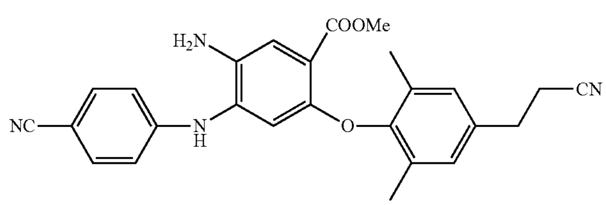 [SMILES: COC(=O)c1cc(N)c(Nc2ccc(C#N)cc2)cc1Oc1c(C)cc(CCC#N)cc1C] |
| 6 | 5-(4''-cyanoethyl-2'', 6''-dimethylphenoxy)-N$^1$-(4'-cyanophenyl)-4-hydroxymethyl-1,2-phenylenediamine | 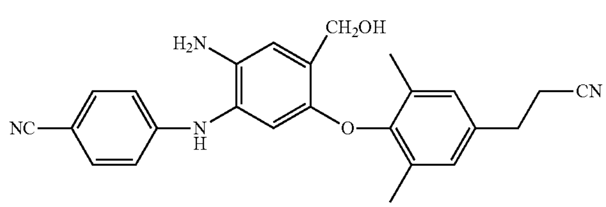 [SMILES: Cc1cc(CCC#N)cc(C)c1Oc1cc(Nc2ccc(C#N)cc2)c(N)cc1CO] |

TABLE 1-continued

Some compounds of the invention

| Compound No. | Name |
|---|---|
| 8 | 4-carboxyl-5-(4''-cyanoethyl-2'', 6''-dimethylphenoxy)-N$^1$-(4'-cyanophenyl)-1,2-phenylenediamine |
| 10 | 4-carbamoyl-N$^1$-(4'-cyanophenyl)-5-(4''-cyanoethyl-2'', 6''-dimethylphenyoxy)-1,2-phenylenediamine |
| 12 | 5-(4''-cyanoethyl-2'', 6''-dimethylphenoxy)-N$^1$-(4'-cyanophenyl)-4-(N-methyl-carbamoyl)-1,2-phenylenediamine |
| 14 | 5-(4''-cyanoethyl-2'', 6''-dimethylphenoxy)-N$^1$-(4'-cyanophenyl)-4-aminosulfonyl-1,2-phenylenediamine |
| 16 | N$^2$-(4-cyanoanilinyl)-6-(2,6-dimethyl-4-propylphenoxy)-3-aminopyridine |
| 17 | N-(4'-cyanophenyl)-5-(4''-hydroxymethyl-2'', 6''-dimethylphenoxy)-4-hydroxymethyl-2-nitroaniline |
| 18 | N$^1$-(4'-cyanophenyl)-5-(4''-hydroxymethyl-2'', 6''-dimethylphenoxy)-4-hydroxymethyl-1,2-phenylenediamine |

TABLE 1-continued

Some compounds of the invention

| Compound No. | Name |
|---|---|
| 21 | N²-(4-cyanoanilinyl)-6-(2,6-difluoro-4-cyanoethyl-phenoxy)-3-aminopyridine |
| 23 | N²-(4-cyanoanilinyl)-6-(2,6-difluoro-4-methyl propionate-phenoxy)-3-aminopyridine |
| 24 | N²-(4-cyanoanilinyl)-6-(2,6-difluoro-4-(3-hydroxypropyl)phenoxy)-3-aminopyridine |
| 26A | 6-(2-bromo-4-cyanoethyl-5-methoxy)phenoxy-2-(4-cyanoanilinyl)-3-aminopyridine |
| 26B | 6-(2-bromo-4-cyanovinyl-5-methoxy)phenoxy-2-(4-cyanoanilinyl)-3-aminopyridine |
| 28 | 2-(4-cyanoanilinyl)-6-(2,6-dibromo-4-cyanoethyl)phenoxy-3-aminopyridine |
| 30 | N²-(4-cyanoanilinyl)-6-(2,6-difluoro-4-butanoylphenoxy)-3-aminopyridine |

TABLE 1-continued

Some compounds of the invention

| Compound No. | Name |
|---|---|
| 33 | $N^1$-(4'-cyanophenyl)-5-(4''-cyanovinyl-2'', 6''-dimethylphenoxy)-4-[(2-methoxyethoxy)methyl]-1,2-phenylenediamine |
| 34 | $N^1$-(4'-cyanophenyl)-5-(4''-cyanoethyl-2'', 6''-dimethylphenoxy)-4-[N-cyclopropylaminomethyl]-1,2-phenylenediamine |
| 35 | $N^1$-(4'-cyanophenyl)-5-(4''-cyanoethyl-2'', 6''-dimethylphenoxy)-1,2,4-triaminobenzene |
| 36 | $N^1$-(4'-cyanophenyl)-5-(4''-cyanoethyl-2'', 6''-dimethylphenoxy)-4-formhydrazide-1,2-phenylenediamine |
| 37 | 4-acetyloxymethyl-$N^1$-(4'-cyanophenyl)-5-(4''-cyanoethyl-2'', 6''-dimethylphenoxy)-1,2-phenylenediamine |
| 38 | $N^1$-(4'-cyanophenyl)-5-(4''-cyanoethyl-2'', 6''-dimethylphenoxy)-4-[methoxymethyl]-1,2-phenylenediamine |

TABLE 1-continued

Some compounds of the invention

| Compound No. | Name | Structure |
|---|---|---|
| 39 | $N^1$-(4'-cyanophenyl)-5-(4''-cyanoethyl-2'', 6''-dimethylphenoxy)-4-cyclopropionyloxymethyl-1,2-phenylenediamine | 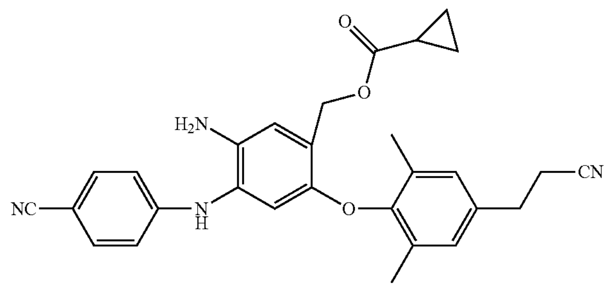 [SMILES: Cc1cc(CCC#N)cc(C)c1Oc1cc(Nc2ccc(C#N)cc2)c(N)cc1COC(=O)C1CC1] |
| 40 | $N^1$-(4'-cyanophenyl)-5-(4''-cyanoethyl-2'', 6''-dimethylphenoxy)-4-[N,N-dimethylaminomethyl]-1,2-phenylenediamine | 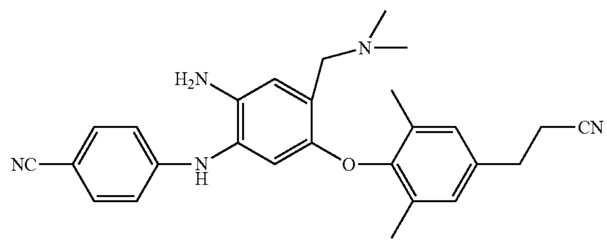 [SMILES: Cc1cc(CCC#N)cc(C)c1Oc1cc(Nc2ccc(C#N)cc2)c(N)cc1CN(C)C] |
| 41 | $N^1$-(4'-cyanophenyl)-5-(4''-cyanoethyl-2'', 6''-dimethylphenoxy)-4-(N-ethylformamido)-1,2-phenylenediamine | 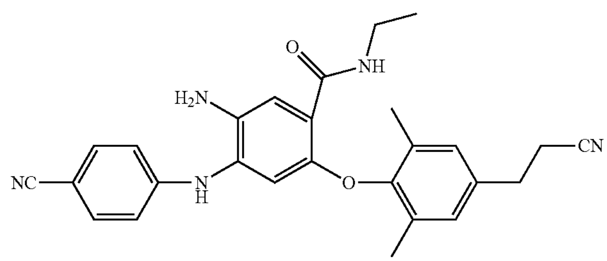 [SMILES: CCNC(=O)c1cc(N)c(Nc2ccc(C#N)cc2)cc1Oc1c(C)cc(CCC#N)cc1C] |
| 42 | 5-(4''-cyanoethyl-2'', 6''-dimethylphenoxy)-$N^1$-(4'-cyanophenyl)-4-(N,N-dimethylformamido)-1,2-phenylenediamine | 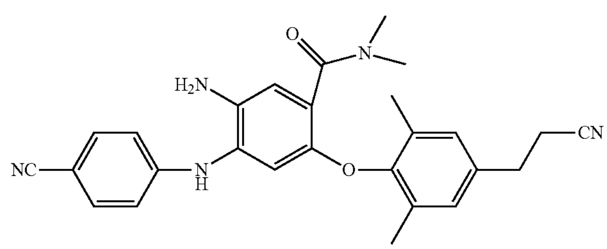 [SMILES: Cc1cc(CCC#N)cc(C)c1Oc1cc(Nc2ccc(C#N)cc2)c(N)cc1C(=O)N(C)C] |
| 43 | $N^1$-(4'-cyanophenyl)-5-(4''-cyanoethyl-2'', 6''-dimethylphenoxy)-4-(N-cyclopropylformamido)-1,2-phenylenediamine | 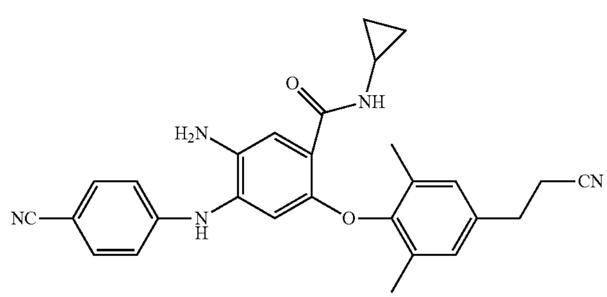 [SMILES: Cc1cc(CCC#N)cc(C)c1Oc1cc(Nc2ccc(C#N)cc2)c(N)cc1C(=O)NC1CC1] |

The compound according to the invention may be used directly or in a form of a pharmaceutically acceptable salt or a solvate thereof. A pharmaceutically acceptable salt of the compound according to the invention includes a conventional salt formed with a pharmaceutically acceptable inorganic or organic acid, or inorganic or organic base. Examples of suitable acid addition salts include salts formed by hydrochloric acid, hydrobromic acid, sulphuric acid, phosphoric acid, nitric acid, perchloric acid, fumaric acid, acetic acid, propionic acid, succinic acid, glycolic acid, formic acid, lactic acid, maleic acid, tartaric acid, citric acid, pamoic acid, malonic acid, hydroxymaleic acid, toluylic acid, glutamic acid, benzoic acid, salicylic acid, fumaric acid, toluene sulfonic acid, methylsulfonic acid, naphthalene-2-sulfonic acid, benzenesulfonic acid, naphtholcarboxylic acid, hydriodic acid, malic acid, tannin, and the like. Examples of suitable base addition salts include salts formed by Na, Li, K, Mg, Al, Ca, Zn, N,N'-dibenzylethylenediamine, chloro-substituted procaine, choline, diethanol amine, ethanediamine, N-methylglucosamine, procaine and the like. When the compound according to the invention is mentioned, it refers to the compound according to the invention and a pharmaceutically acceptable salt or solvate thereof.

In another aspect, the invention relates to a method for preparing a compound according to any item of the invention. The scheme is shown as follows:

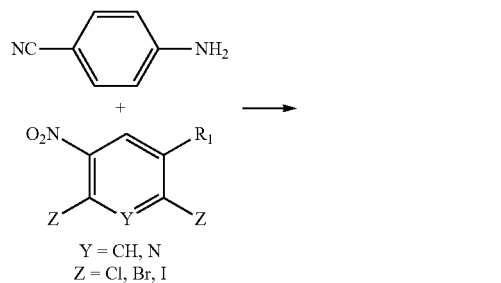

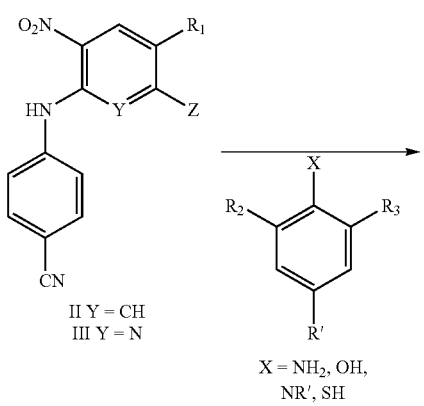

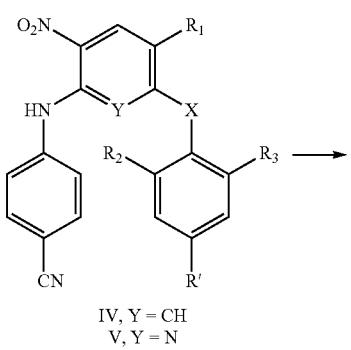

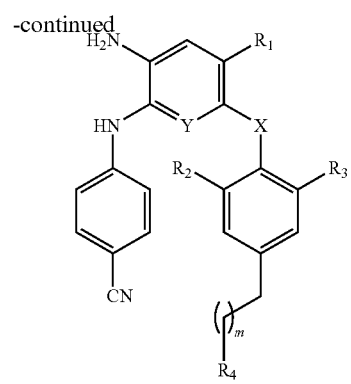

Y = CH, N
X = NH, O, NR', S wherein $R_1, R_2, R_3, R_4$, X and Y, and m are defined as they are in any of the preceding items; the method comprises reacting a substituted 2,6-dihalo benzene or pyridine compound with a p-substituted aniline compound under basic ($K_2CO_3$) condition, or using excessive 4-cyano aniline to carry out a solvent-free reaction to produce the intermediate of formula II or III; coupling with a 1,3,5-trisubstituted phenol or aniline compound under basic ($K_2CO_3$, $Cs_2CO_3$, NaH or potassium t-butoxide) condition to get an intermediate (IV or V) having a tricycle backbone structure, then converting the substituent ($R_1$) of the intermediate ring to the corresponding group through conventional functional-group conversion reaction (such as oxidization, reduction, substitution or coupling), and finally reducing the nitro group on the intermediate ring to an amino group.

In a further aspect, the invention relates to a pharmaceutical composition, comprising the compound or pharmaceutically acceptable salt thereof according to any item of the invention; optionally, the pharmaceutical composition further comprises one or more pharmaceutically acceptable carrier or excipients.

The term "composition" refers to a product comprising specified ingredients in specified amounts, and a product generated from direct or indirect combination of specified amounts of specified ingredients.

The pharmaceutical composition according to the invention generally comprises 0.1-90 wt % of the compound and/or pharmaceutically acceptable salt thereof according to the invention. The pharmaceutical composition may be prepared according to methods known in the art. For this purpose, if necessary, the compound and/or pharmaceutically acceptable salt thereof according to the invention may be combined with one or more solid or liquid pharmaceutical excipient and/or adjuvant to prepare an administration form or dosage form suitable for use in human.

The compounds according to the invention or the pharmaceutical compositions comprising the same may be administered in a unit dosage form, and the administration route may be enteric or parenteral, such as oral, muscular, subdermal, rhinal, buccal, dermal, peritoneal or rectal, etc. The dosage forms are, for example, tablets, capsules, drop pills, aerosols, pills, powder, liquores, suspensions, emulsion, granules, liposomes, cutaneous permeable agents, buccal tablets, suppositories, lyophilized powder-injections, etc. They may be conventional preparations, sustained release preparations, controlled release preparations, and various microparticle drug delivery systems. In order to formulate a unit dosage form into a table, a variety of carriers known in the art may be widely used. Examples of carriers are, for example, diluents and absorbents, such as starch, dextrin, calcium sulfate, lactose, mannitol, sucrose, sodium chloride, glucose, urea, calcium carbonate, kaoliang oil, microcrystalline cellulose, aluminium silicate and the like; wetting agents and binding agents, such as water, glycerol, polyethylene glycol, ethanol, propanol, starch paste, dextrin, syrup, honey, glucose solution, mucilago acaciae, gelatin slurry, carboxymethylcellulose sodium, shellack, methylcellulose, potassium phosphate, polyvinylpyrrolidone, etc.; disintegrating agents, such as dry starch, alginate, powdered agar, laminaran, dicarbonate and citric acid, calcium carbonate, polyoxyethylene, sorbitan fatty acid ester, sodium dodecylsulphate, methylcellulose, ethyl cellulose, etc.; disintegration inhibitor, such as sucrose, tristearin, cacao butter, hydrogenated oil, etc.; absorption enhancers, such as quaternary ammonium salt, sodium dodecylsulphate, etc.; lubricants, such as talcum powder, silicon dioxide, corn starch, stearate, boric acid, liquid paraffin, polyethylene glycol, etc. The tablets may be further formulated into coated tablets, such as sugar coated tablet, film coated tablet, enteric-coated tablet, or bilayered tablets and multilayered tablets. In order to formulate a unit dosage form into a pill, a variety of carriers known in the art may be widely used. Examples of carriers are, for example, diluents and absorbents, such as glucose, lactose, starch, cacao butter, hydrogenated vegetable oil, polyvinylpyrrolidone, Gelucire, kaolin, talcum powder, etc.; binding agents such as Arabic gum, bassora gum, gelatin, ethanol, honey, liquid sugar, rice paste or panada, etc.; disintegrating agents, such as powdered agar, dry starch, alginate, sodium dodecylsulphate, methylcellulose, ethyl cellulose, etc. In order to formulate a unit dosage form into a suppository, a variety of carriers known in the art may be widely used. Examples of carriers are, for example, polyethylene glycol, lecithin, cacao butter, higher alcohols, esters of higher alcohols, gelatin, semi-synthesized glyceride, etc. In order to formulate a unit dosage form into a capasule, a compound or a pharmaceutically acceptable salt thereof as an active ingredient is mixed with said carriers, and the resultant mixture is placed in a hard gelatine capsule or a soft capsule. A compound or a pharmaceutically acceptable salt thereof as an active ingredient may be formulated into a microcapsule, may be suspended in an aqueous media to form a suspension, which may be packaged into a hard capsule or formulated into an injection. In order to formulate a unit dosage form into a formulation for use in injection, such as a liquor, an emulsion, lyophilized powder-injection and suspension, all the common diluents may be used in the art, for example, water, ethanol, polyethylene glycol, 1,3-propanediol, ethoxylated isooctadecanol, polyoxylated isooctadecanol, polyoxyethylene sorbitan fatty acid esters, etc. In addition, in order to prepare isotonic injection, a suitable amount of sodium chloride, glucose, or glycerol may be added to the formulation for use in injection. In addition, conventional cosolvents, buffers, pH regulators and the like may be added.

In addition, if necessary, to a pharmaceutical formulation, colorants, preservatives, flavors, flavoring agents, sweeteners or other materials may also be added.

The administration dose of the compound or pharmaceutically acceptable salt thereof according to the invention depends on many factors, e.g. the nature and severity of the diseases to be prevented or treated, gender, age, weight and individual response of a patent or animal, the particular compound used, the administration route and administration frequency, and the like. Said dose may be administered in one single dose or in several doses, such as in two, three or four doses.

The actual dosage level of the active ingredient in the pharmaceutical composition according to the invention may be altered so that the amount of the active compound is effective to obtain a desired treatment response in the case of a particular patient, a particular composition and a particular administration route. The dosage level is selected depending on the activity of a particular compound, the administration route, the severity of the disease to be treated, and the condition and the medical history of the patient to be treated. However, the general method in the art is that the dosage of a compound starts from a level lower than the one needed for the desired therapeutic effect, and increases gradually until the desired effect is obtained.

In a further aspect, the invention relates to use of the compound or pharmaceutically acceptable salt thereof according to any item of the invention in manufacture of a medicament for prevention and/or treatment and/or assistant treatment of HIV or a disease or a condition associated with HIV infection.

In a further aspect, the invention relates to a method for prevention and/or treatment and/or assistant treatment of HIV or a disease or a condition associated with HIV infection, comprising the step of administering to a subject an effective amount of the compound or pharmaceutically acceptable salt thereof according to any item of the invention.

In a further aspect, the invention relates to use of the compound or pharmaceutically acceptable salt thereof according to any item of the invention in manufacture of a medicament or an agent for inhibiting HIV virus.

In a further aspect, the invention relates to a method for inhibiting HIV virus in vivo or in vitro, comprising the step of administering an effective amount of the compound or pharmaceutically acceptable salt thereof according to any item of the invention.

The term "an amount effective for prevention and/or treatment of a compound according to the invention" refers to an amount of a compound sufficient for the treatment of disorders in a reasonable effect/risk ratio suitable for any medical prevention and/or treatment.

The term "subject" may refer to a patient or an animal that receives the composition according to the invention to treat, prevent, ease and/or alleviate the disease or condition according to the invention, particularly a mammal, e.g. human, dog, monkey, cattle, horse, etc.

The term "disease and/or condition" refers to a physical state of the subject, which is associated with the disease and/or condition of the invention.

It should be understood that the total daily amount of a compound or a pharmaceutical composition according to the invention shall be decided by an attending physician within a reliable medical range. For any specific patient, the therapeutically effective dosage level depends on many factors, including the disorder to be treated and the severity of the disorder; the activity of the particular compound used; the particular composition used; age, weight, general health condition, gender and diet of the patient; the administration timing, administration route and excretion rate of the particular compound used; the duration of the treatment; drugs used in combination or coincidental with the specific compound employed; and similar factors well known in medical field. For example, the general method in the art is that the dosage of a compound starts from a level lower than the one needed for the desired therapeutic effect, and increases gradually until the desired effect is obtained. In general, the dosage of a compound according to the invention for a mammal, particularly human, is between 0.001 and 1000 mg/kg weight/day, e.g. between 0.01 and 100 mg/kg weight/day, e.g. between 0.01 and 10 mg/kg weight/day.

The compounds according to the invention may effectively prevent and/or treat the diseases or conditions as described in the invention.

In the invention,

The term "$C_{1-6}$ alkyl" refers to a linear or branched alkyl having 1-6 carbon atoms, e.g. methyl, ethyl, propyl, isopropyl, n-butyl, sec-butyl, tert-butyl, amyl, 2-amyl, isoamyl, neo-amyl, hexyl, 2-hexyl, 3-hexyl, etc.; $C_{1-3}$alkyl may be understood in a similar manner. $C_{1-3}$alkyl is preferred.

The term "$C_{1-6}$ alkoxy" refers to a linear or branched alkoxy having 1-6 carbon atoms, e.g. methoxy, ethoxyl, propoxy, isopropoxy, n-butoxy, sec-butoxy, tert-butoxy, pentyloxy, 2-pentyloxy, isoamoxy, neopentyloxy, hexyloxy, 2-hexyloxy, 3-hexyloxy etc.; $C_{1-3}$ alkoxy may also be understood in the same manner. $C_{1-3}$alkoxy is preferred.

The term "$C_{3-8}$ cycloalkyl" refers to a saturated carbon ring group having 3-8 carbon atoms. The cycloalkyl may be a monocycle or a polycyclic fused system, and may be fused to an aromatic ring. The examples of these groups include cyclopropyl, cyclobutyl, cyclopentyl and cyclohexyl. $C_{3-6}$ cycloalkyl may also be understood in the same manner. Cycloalkyl used herein may be not substituted or be substituted with various groups at one or more substitutable positions as described in detail. For example, these cycloalkyl may be optionally substituted by a group selected from the following: $C_{1-6}$ alkyl, $C_{1-6}$ alkoxy, cyano, halogen, hydroxyl, amino group, nitro group, mono($C_{1-6}$)alkylamino, di($C_{1-6}$)alkylamino, $C_{2-6}$ alkenyl, $C_{2-6}$ alkynyl, $C_{1-6}$ haloalkyl, $C_{1-6}$ haloalkoxy.

The term "$C_{1-6}$ acyl" refers to —C(O)R', wherein R' is selected from $C_{1-6}$ alkyl or $C_{3-8}$ cycloalkyl as defined in the invention, and typical examples of acyl include, but are not limited to —C(O)CH$_3$, —C(O)C$_2$H$_5$, etc.

The term "$C_{1-6}$ ester group" refers to —C(O)OR', wherein R' is selected from $C_{1-6}$ alkyl and $C_{3-8}$ cycloalkyl as defined in the invention, and typical examples of ester group include, but are not limited to —COOCH$_3$, —COOC$_2$H$_5$, etc.

The term "$C_{1-6}$ acyloxy" refers to —OC(O)R', wherein R' is selected from $C_{1-6}$ alkyl and $C_{3-8}$ cycloalkyl as defined in the invention, and typical examples thereof include, but are not limited to —OC(O)CH$_3$, —OC(O)C$_2$H$_5$, etc.

The term "$C_{1-6}$ hydroxyalkyl" refers to $C_{1-6}$ alkyl having one or more hydroxyl groups at one or more carbon atoms thereof. $C_{1-4}$ hydroxyalkyl may also be understood in the same manner.

The term "$C_{1-6}$ haloalkyl" refers to $C_{1-6}$ alkyl having one or more halogen atoms at one or more carbon atoms thereof; when more halogen atoms are comprised, the halogen atoms may be identical or different. $C_{1-4}$ haloalkyl may also be understood in the same manner.

The term "halogen" or "halogen atom" refers to fluorine, chlorine, bromine and iodine.

The term "$C_{1-6}$ aminoalkyl" refers to $C_{1-6}$ alkyl having one or more amino groups at one or more carbon atoms thereof. $C_{1-4}$ aminoalkyl may also be understood in the same manner.

The term "$C_{1-6}$ ether alkyl" refers to $C_{1-6}$ alkyl having one or more oxygen atoms inserted between any two carbon atoms thereof. $C_{1-4}$ ether alkyl may also be understood in the same manner.

The term "$C_{1-6}$ cyanoalkyl" refers to $C_{1-6}$ alkyl having one or more cyano inserted between any two carbon atoms thereof. $C_{1-4}$ cyanoalkyl may also be understood in a similar manner.

The term "$C_{1-6}$ hydroxyalkoxy" refers to a group —OR', wherein R' is $C_{1-6}$ alkyl having one or more hydroxyl groups at one or more carbon atoms thereof.

The term "$C_{1-6}$ haloalkoxy" refers to a group —OR', wherein R' is $C_{1-6}$ alkyl having one or more halogen atoms at one or more carbon atoms thereof.

The term "$C_{1-6}$ aminoalkoxy" refers to a group —OR', wherein R' is $C_{1-6}$ alkyl having one or more amino groups at one or more carbon atoms thereof.

The term "$C_{1-6}$ ether alkoxy" refers to a group —OR', wherein R' is $C_{1-6}$ alkyl having one or more oxygen atoms inserted between any two carbon atoms thereof.

The term "$C_{1-6}$ alkylamino" refers to NHR', wherein R' is selected from $C_{1-6}$ alkyl or $C_{3-8}$ cycloalkyl as defined in the invention.

The term "$C_{1-6}$ ether alkylamino" refers to NHR', wherein R' is selected from $C_{1-6}$ alkyl or $C_{3-8}$ cycloalkyl as defined in the invention, and has one or more oxygen atoms inserted between any two carbon atoms of $C_{1-6}$ alkyl or $C_{3-8}$ cycloalkyl.

The term "$C_{1-6}$ dialkylamino" refers to NR'R", wherein R' and R" each are independently selected from $C_{1-6}$ alkyl and $C_{3-6}$cycloalkyl as defined in the invention.

The term "$C_{2-6}$ alkenyl" refers to an alkenyl having 2-6 carbon atoms and at least one double bond, including vinyl, propenyl, 1-buta-3-enyl, 1-penta-3-enyl etc.; $C_{3-5}$ alkenyl may be understood in a similar manner. $C_{3-5}$ alkenyl is preferred.

The term "$C_{2-6}$ alkynyl" refers to an alkyl having 2-6 carbon atoms and at least one triple bond, including ethynyl, propinyl, butynyl, pentyn-2-yl etc.; $C_{3-5}$ alkynyl may also be understood in a similar manner. $C_{3-5}$ alkynyl is preferred.

The term "halogen" refers to fluorine, chlorine, bromine, and iodine atom.

The term "$C_{3-8}$ cyclyl" in "$C_{3-8}$ cyclylalkoxy", "$C_{3-8}$ cyclylalkylamino" refers to a saturated or unsaturated carbon ring group having 3-8 carbon atoms. In one embodiment of the invention, $C_{3-8}$ cyclyl refers to $C_{3-8}$ cycloalkyl.

The term "heterocycyl" or "heterocyclyl" refers to one or more 5-membered, 6-membered or 7-membered carbon cyclic systems, including a fused cyclic system having 4-10 atoms, wherein the cyclic system contains at least one and at most four heteroatoms selected from nitrogen, oxygen or sulphur, provided that the ring of the group does not contain two contiguous O or S atoms. A fused cyclic system may be a heterocycle fused to an aromatic group. The preferred heterocycyl includes, but is not limited to, pyrrolidinyl, tetrahydrofuranyl, dihydrofuranyl, tetrahydrothienyl, piperidyl, morpholinyl ring, cyclohexyl ring, piperazine ring, etc., which may be substituted with the following groups: $C_{1-6}$ alkyl, $C_{1-6}$ alkoxy, cyano, halogen, hydroxyl, amino, nitro, mono($C_{1-6}$)alkylamino, di($C_{1-6}$)alkylamino, $C_{2-6}$ alkenyl, $C_{2-6}$ alkynyl, $C_{1-6}$ haloalkyl, $C_{1-6}$ haloalkoxy. Preferably, the heterocyclyl is a 3- to 8-membered heterocyclyl, more preferably a 5- to 8-membered heterocyclyl.

The term "heterocyclylalkyl" refers to $C_{1-6}$ alkyl (as defined above) substituted with heterocyclyl (as defined above). 3- to 8-membered heterocyclylalkyl or 3- to 5-membered heterocyclylalkyl is preferred. More preferred heterocyclylalkyl is 5-membered or 6-membered heterocyclyl-$C_{1-3}$-alkyl. The example includes tetrahydropyranylmethyl.

The term "heterocyclylalkylamino" refers to heterocyclyl (as defined above) substituted with aminoalkyl (as defined above) (e.g. $C_{1-6}$ aminoalkyl or $C_{1-4}$ aminoalkyl or $C_{1-3}$ aminoalkyl). 3- to 8-membered heterocyclylalkylamino or 3- to 5-membered heterocyclylalkylamino are preferred.

The term "heterocyclylalkoxy" refers to heterocyclyl (as defined above) substituted with alkoxy (as defined above)

(e.g. $C_{1-6}$alkoxy or $C_{1-4}$alkoxy or $C_{1-3}$alkoxy). 3- to 8-membered heterocyclylalkoxy or 3- to 5-membered heterocyclylalkoxy are preferred.

The term "cycloalkylalkyl" refers to $C_{1-6}$ alkyl (as defined above) substituted with $C_{3-8}$ cycloalkyl (as defined above). More preferred heterocyclyl is 5-membered or 6-membered cycloalkyl-$C_{1-3}$-alkyl. The example includes cyclopropylmethyl.

Advantageous Effects of the Invention

The compounds according to the invention have strong inhibitory activity (at nM level) against wild-type and various drug-resistant HIV viral strains and exhibit good druggability. The novel compounds according to the invention have high efficiency, low toxicity, good solubility, log P value (<5) and metabolic stability ($t_{1/2}$), all of which facilitate the absorption of the drug in vivo and generation of a better effect. The compounds according to the invention are potential to be anti-HIV drugs.

SPECIFIC MODES FOR CARRYING OUT THE INVENTION

The embodiments of the invention are described by combining the following examples. However, a person skilled in the art understands that the following examples are only intended to describe the invention, and should not be regarded as defining the scope of the invention. In the case where the concrete conditions are not indicated in the examples, the examples are carried out according to conventional conditions or the conditions recommended by the manufacturer. The reagents or apparatuses, the manufacturers of which are not indicated, are the conventional products that are commercially available.

Firstly, according to the following preparation examples 1-3, nitro target compound is prepared, and then is reduced to obtain the amino target compound. The scheme is as follows:

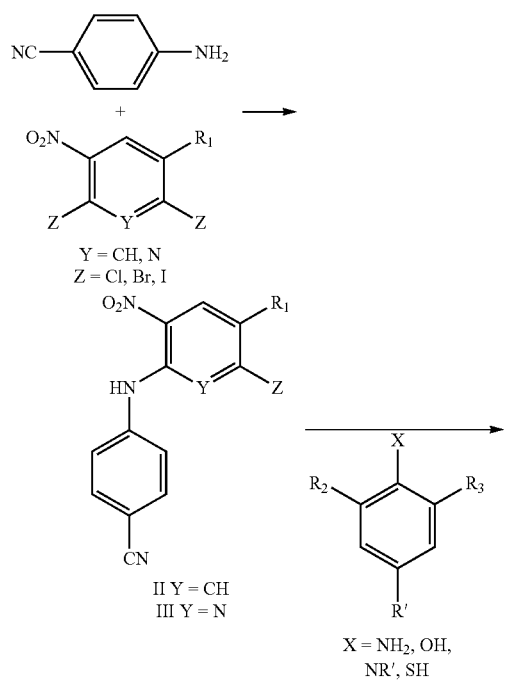

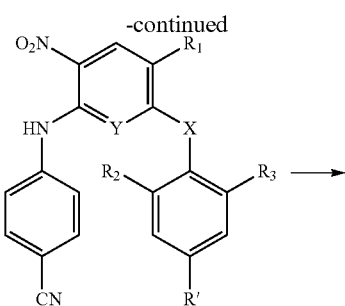

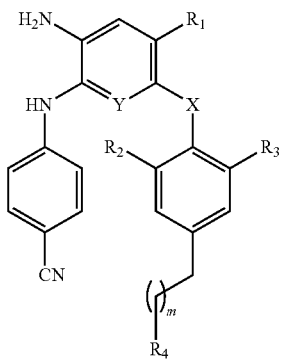

Preparation Example 1

Preparation of 5-chloro-N-(4-cyanophenyl)-2-nitro-4-substituent (R) aniline (Intermediate I) or 6-chloro-3-nitro-2-(4-cyanoanilinyl)pyridine (Intermediate II)

Method A. 2,4-dichloro-5-substituent nitrobenzene (1 equiv) and 4-cyanoaniline (1.1 equiv) were dissolved in DMF (3 ml), and under the condition of ice bath, potassium t-butoxide was added in batches, and the resultant solution was stirred for about 1 h at room temperature. The reaction solution was poured into ice-water, the pH was adjusted to about 6 with 5% aqueous hydrochloric acid solution, and yellow precipitates formed. The mixture was filtered, washed with water until it was neutral, dried, and isolated and purified through medium pressure column, to get pure intermediate I.

Method B. 2,6-dichloro-3-nitropyridine (10 mmol) and 4-cyanoaniline (12 mmol) were placed in a reaction bottle; the reaction took place in nitrogen atmosphere at 140° C. for 4 h. The reaction solution was poured into ice-water, pH was adjusted to 2-3, yellow solid was precipitated, filtered, washed with water, and dried to get a crude product. 95% ethanol was used to recrystallize it to get the corresponding intermediate II, with a yield of 73%, mp 175-8° C.

Preparation Example 2

Preparation of $N^1$-(4'-cyanophenyl)-5-(4"-substituted-2",6"-dimethylphenoxy)-4-substituent-2-nitroaniline (IV)

Method A: intermediate I or intermediate II (1 equiv) and 4-substituent-2,6-dimethylphenol (1.2 equiv) were dissolved in DMF (2-5 ml), and anhydrous potassium carbonate (2 equiv) or cesium carbonate was added; the reaction lasted for 15 min at 190° C. under microwave. The reaction solution was poured into a suitable amount of ice-water; pH was adjusted to be neutral with 5% hydrochloric acid solution; the resultant solution was extracted with ethyl acetate for three times; the organic phase was dried with anhydrous sodium sulfate and was dried under rotation to get the crude product of the corresponding diarylnitrobenzene intermediate IV or diarylnitropyridine intermediate V. The crude product was isolated and purified through medium pressure column (petroleum ether/dichloromethane).

Method B: said reactants and reagents were reacted in an oil-bath at 130° C. for about 5 h, and the post-treatment was carried out as described above. Intermediate IV or intermediate V was obtained.

Method C: 266 mg (1.5 mmol) of $(EtO)_2P(O)CH_2CN$ was dissolved in 15 mL of THF, cooled in an ice-water bath, and stirred; 168 mg (1.5 mmol) of t-BuOK was added, and the resultant solution was stirred for 30 min. The reaction solution was transferred at room temperature and was further stirred for 30 min. 1 mmol of formyl-containing intermediate V was dissolved in 15 mL of THF, and the resultant solution was added dropwise to said reaction bottle at room temperature. After stirring for 2-6 h, the reaction was stopped. The reaction solution was poured into 100 mL of water, stirred, and extracted with ethyl acetate (50 mL×3). The organic phase was dried over anhydrous sodium sulfate, concentrated, and isolated through a flash preparative column chromatography to get the corresponding product (intermediate IV or intermediate V) (eluent: dichloromethane/petroleum ether=0-100%, 200-300 mush silica gel).

Preparation Example 3

The Reduction Method for Preparation of Diarylanilines or Diarylpyridinamines

Method A (catalytic hydrogenation): diaryl nitrobenzene or diaryl nitropyridine (1 mmol) was placed in anhydrous ethanol (30 mL), an excessive amount of Pd/C (5%) was added, and the resultant mixture was shaked for about 2 h (or until no hydrogen gas was absorbed) at a pressure of 30-40 p.s.i. after hydrogen gas was introduced, and then the reaction was stopped. The resultant mixture was filtered to remove the catalyst, and the filtrate was washed with ethanol for several times, and the crude product obtained after concentrating of the filtrate was isolated through a column chromatography (eluent is $MeOH/CH_2Cl_2$), to get the corresponding diarylaniline or diarylpyridinamine compound.

Method B (selective reduction reaction): to a mixed solution of diaryl nitrobenzene or diaryl nitropyridine (1 mmol) in THF and water (30 mL, v/v 1:1), a small amount of aqueous ammonia (25%) was added, and an 10-fold amount of sodium hydrosulfite was added in batches to the reaction bottle. The reaction finished after stirring the reaction solution at room temperature for about 2 h. The reaction solution was poured into ice-water, extracted with ethyl acetate, and isolated; the organic solvent was removed, and the crude product was isolated through a chromatographic column (eluent is $MeOH/CH_2Cl_2$) to get the corresponding diarylaniline or diarylpyridinamine compound as desired.

Example 1

Preparation of 5-(4"-cyanovinyl-2",6"-dimethylphenoxy)-$N^1$-(4'-cyanophenyl)-4-trifluoromethyl-2-nitroaniline (Compound 1)

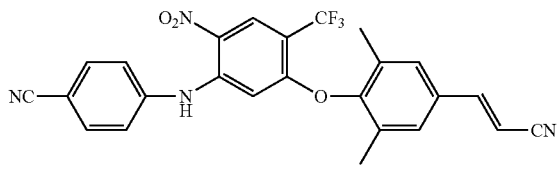 [SMILES: Cc1cc(/C=C/C#N)cc(C)c1Oc1cc(Nc2ccc(C#N)cc2)c([N+](=O)[O-])cc1C(F)(F)F]

4-cyano aniline (130 mg, 1.1 mmol) and 2,4-dichloro-5-nitrobenzotrifluoride (260 mg, 1 mmol) were used as starting materials. A general synthetic method of intermediate I was employed to get 5-chloro-N-(4-cyanophenyl)-2-nitro-4-trifluoromethylaniline (I-1) (281 mg) with a yield of 82%, as a yellow solid, and with a melting point of 180-182° C.; MS m/z (%) 359.2 (M+$NH_4$, 100). I-1 and 4"-formyl-2",6"-dimethylphenol were coupled by Method A in Preparation Example 2. The product was dissolved in 15 mL of THF, and was reacted with $(EtO)_2P(O)CH_2CN$ (1.5 mmol) and an equivalent mole of potassium t-butoxide in THF by Method C in Preparation Example 2 under stirring for about 3 h. The product obtained by conventional post-treatment was isolated and purified through medium pressure column (dichloromethane/methanol) to get Compound 1, with a melting point of 248-250° C. and a yield of 87%. $^1$H NMR δ ppm 2.15 (6H, s, 2×$CH_3$), 5.85 (1H, d, J=16.4 Hz, =CH), 6.27 (1H, s, ArH-6), 7.10 (2H, d, J=8.8 Hz, ArH-2',6'), 7.21 (2H, s, ArH-3",5"), 7.32 (1H, d, J=16.4 Hz, CH=), 7.52 (2H, d, J=8.8 Hz, ArH-3',5'), 8.67 (1H, s, ArH-3), 9.91 (1H, s, NH); MS m/z (%) 501.1 (M+Na, 100).

Example 2

Preparation of 5-(4"-cyanoethyl-2",6"-dimethylphenoxy)-$N^1$-(4'-cyanophenyl)-4-trifluoromethyl-1,2-phenylenediamine (Compound 2)

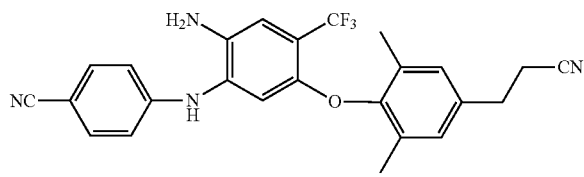 [SMILES: Cc1cc(CCC#N)cc(C)c1Oc1cc(Nc2ccc(C#N)cc2)c(N)cc1C(F)(F)F]

Compound 1 was subjected to catalytic hydrogenation with 5-10% Pd/C in anhydrous ethanol at a pressure of 30-80 p.s.i. (Method A in Preparation Example 3). After reaction for about 2 h, Pd/C was filtered out, the solvent was removed under reduced pressure, and purification was carried out through medium pressure column (dichloromethane/methanol, gradient elution) to get Compound 1 with a yield of 31% as a brown solid. $^1$H NMR ($CDCl_3$) δ ppm 2.11 (6H, s, 2×$CH_3$), 2.61 (2H, t, J=7.2 Hz, $CH_2CN$), 2.87 (2H, t, J=7.2 Hz, Ar$CH_2$), 5.72 (1H, s, NH), 6.20 (1H, s, ArH-6), 6.64 (2H, d, J=8.8 Hz, ArH-2',6'), 6.94 (2H, s, ArH-3",5"), 7.14 (1H, s, ArH-3), 7.44 (2H, d, J=8.8 Hz, ArH-3',5'); MS m/z (%) 451.1 (M+1, 100).

Example 3

Preparation of 5-(4"-cyanovinyl-2",6"-dimethylphenoxy)-$N^1$-(4'-cyanophenyl)-4-methoxycarbonyl-2-nitroaniline (Compound 3)

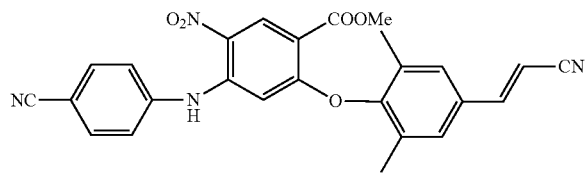 [SMILES: COC(=O)c1cc([N+](=O)[O-])c(Nc2ccc(C#N)cc2)cc1Oc1c(C)cc(/C=C/C#N)cc1C]

4-cyano aniline and 2,4-dichloro-5-methoxycarbonyl-nitrobenzene as starting materials were coupled by Method A in Preparation Example 1 to get intermediate I-2[4-chloro-$N^2$-(4'-cyanophenyl)-5-methoxycarbonyl-nitrobenzene]. I-2 was coupled with 2,6-dimethyl-4-formylphenol by Method A in Preparation Example 2, and was subjected to acrylcyanidation (Method C) to get Compound 3; with a yield of 88%; yellow solid; m.p. 260-262° C. $^1$H NMR δ ppm 2.16 (6H, s, 2×CH$_3$), 3.96 (3H, s, OCH$_3$), 5.84 (1H, d, J=16.4 Hz, =CH), 6.26 (1H, s, ArH-6), 7.08 (2H, d, J=8.8 Hz, ArH-2',6'), 7.20 (2H, s, ArH-3",5"), 7.32 (1H, d, J=16.4 Hz, CH=), 7.50 (2H, d, J=8.8 Hz, ArH-3',5'), 9.00 (1H, s, ArH-3), 9.87 (1H, s, NH); MS m/z (%) 469.4 (M+1, 100).

Example 4

Preparation of 5-(4"-cyanoethyl-2",6"-dimethylphenoxy)-$N^1$-(4'-cyanophenyl)-4-methoxycarbonyl-1,2-phenylenediamine (Compound 4)

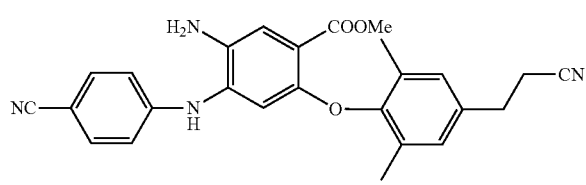 [SMILES: COC(=O)c1cc(N)c(Nc2ccc(C#N)cc2)cc1Oc1c(C)cc(CCC#N)cc1C]

Compound 3 was subjected to catalytic hydrogenation (Method A in Preparation Example 3) to get Compound 4 as a off-white solid (a yield of 47%), with a melting point of 236-238° C. $^1$H NMR δ ppm 2.13 (6H, s, 2×CH$_3$-2",6"), 2.61 (2H, t, —CH$_2$—), 2.87 (2H, t, Ar—CH$_2$—), 3.93 (3H, s, —COOCH$_3$), 5.90 (1H, s, NH), 6.23 (1H, s, ArH-6), 6.69 (2H, d, J=8.8 Hz, ArH-2',6'), 6.93 (2H, s, ArH-3",5"), 7.43 (2H, d, J=8.8 Hz, ArH-3',5'), 7.45 (1H, s, ArH-3). MS m/z (%) 409.2 (M+1, 100).

Example 5

Preparation of $N^1$-(4'-cyanophenyl)-5-(4"-cyanovinyl-2",6"-dimethylphenoxy)-4-hydroxymethyl-2-nitroaniline (Compound 5)

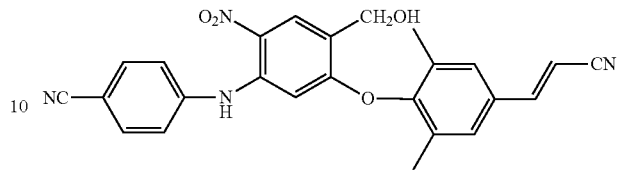

The ester group of Compound 3 was reacted with lithium borohydride (LiBH$_4$) in a mixed solvent of THF and methanol for 1 h, and was reduced to hydroxymethyl to get Compound 5, with a yield of 91%; yellow solid; m.p. 232-234° C.; $^1$H NMR δ ppm 2.15 (6H, s, 2×CH$_3$), 4.89 (2H, s, OCH$_2$), 5.85 (1H, d, J=16.4 Hz, =CH), 6.27 (1H, s, ArH-6), 7.05 (2H, d, J=8.8 Hz, ArH-2',6'), 7.21 (2H, s, ArH-3",5"), 7.28 (1H, d, J=16.4 Hz, CH=), 7.47 (2H, d, J=8.8 Hz, ArH-3',5'), 8.41 (1H, s, ArH-3), 9.70 (1H, s, NH); MS m/z (%) 439.3 (M−1, 100).

Example 6

Preparation of 5-(4"-cyanoethyl-2",6"-dimethylphenoxy)-$N^1$-(4'-cyanophenyl)-4-hydroxymethyl-1,2-phenylenediamine (Compound 6)

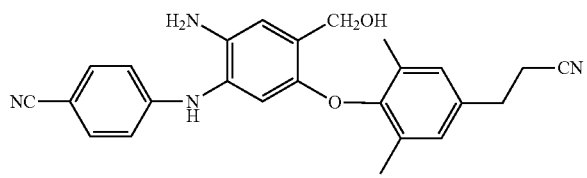 [SMILES: Cc1cc(CCC#N)cc(C)c1Oc1cc(Nc2ccc(C#N)cc2)c(N)cc1CO]

Compound 5 (440 mg, 1 mmol) was subjected to catalytic hydrogenation (Method A in Preparation Example 3) to get Compound 6 (264 mg), with a yield of 64%; off-white solid; with a melting point of 115-117° C.; $^1$H NMR (CDCl$_3$) δ ppm 2.10 (6H, s, 2×CH$_3$), 2.61 (2H, t, J=7.2 Hz, CH$_2$CN), 2.87 (2H, t, J=7.2 Hz, ArCH$_2$), 4.86 (2H, s, CH$_2$O), 5.54 (1H, s, NH), 6.04 (1H, s, ArH-6), 6.55 (2H, d, J=8.8 Hz, ArH-2',6'), 6.91 (1H, s, ArH-3), 6.93 (2H, s, ArH-3",5"), 7.40 (2H, d, J=8.8 Hz, ArH-3',5'); MS m/z (%) 413.4 (M+1, 100).

Example 7

Preparation of 4-carboxyl-5-(4"-cyanovinyl-2",6"-dimethylphenoxy)-$N^1$-(4'-cyanophenyl)-2-nitroaniline (Compound 7)

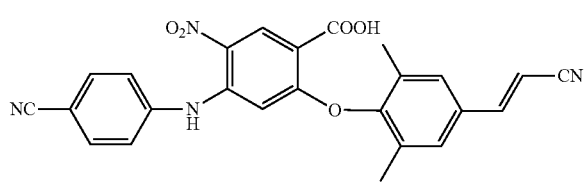

In the presence of aqueous NaOH solution (10%), Compound 3 was reacted in a mixed solvent of methanol and THF at room temperature for 4 h to get Compound 7 (454 mg, 1 mmol), with a yield of 90%; m.p. 262-265° C.; $^1$H NMR (DMSO-d$_6$) δ ppm 2.06 (6H, s, 2×CH$_3$), 5.95 (1H, s, ArH-6), 6.44 (1H, d, J=16.4 Hz, =CH), 7.22 (2H, d, J=8.8 Hz, ArH-2',6'), 7.47 (2H, s, ArH-3",5"), 7.58 (1H, d, J=16.4 Hz, CH=), 7.65 (2H, d, J=8.8 Hz, ArH-2',6'), 8.72 (1H, s, ArH-3), 9.79 (1H, s, NH), 13.21 (1H, s, COOH); MS m/z (%) 453.4 (M−1, 100).

Example 8

Preparation of 4-carboxyl-5-(4"-cyanoethyl-2",6"-dimethylphenoxy)-N$^1$-(4'-cyanophenyl)-1,2-phenylenediamine (Compound 8)

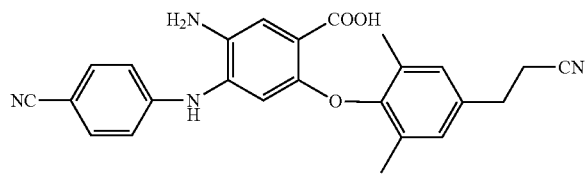 [SMILES: Cc1cc(CCC#N)cc(C)c1Oc1cc(Nc2ccc(C#N)cc2)c(N)cc1C(=O)O]

Compound 7 was subjected to catalytic hydrogenation (Method A in Preparation Example 3) to get Compound 8, with a yield of 33.1%; off-white solid; $^1$H NMR (CDCl$_3$) δ ppm 2.16 (6H, s, 2×CH$_3$), 2.64 (2H, t, J=7.2 Hz, CH$_2$CN), 2.91 (2H, t, J=7.2 Hz, ArCH$_2$), 6.08 (1H, s, NH), 6.31 (1H, s, ArH-6), 6.76 (2H, d, J=8.8 Hz, ArH-2',6'), 7.01 (2H, s, ArH-3",5"), 7.46 (2H, d, J=8.8 Hz, ArH-3',5'), 7.73 (1H, s, ArH-3); MS m/z (%) 425.2 (M−1, 100).

Example 9

Preparation of N$^1$-(4'-cyanophenyl)-5-(4"-cyanovinyl-2",6"-dimethylphenoxy)-4-acylamino-2-nitroaniline (Compound 9)

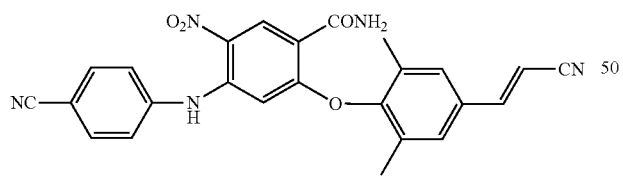

Compound 7 and SOCl$_2$ (0.5 mL) were stirred in anhydrous THF for a moment, aqueous ammonia (25-30%, 1 mL) was added in the condition of an ice bath. The resultant solution was stirred for 30 min, and poured into ice-water to precipitate a solid. The mixture was filtered and isolated through column chromatography to get Compound 9, with a yield of 87%; yellow solid; m.p. 278-280° C.; $^1$H NMR δ ppm 2.16 (6H, s, 2×CH$_3$), 5.88 (1H, d, J=16.4 Hz, =CH), 6.29 (1H, s, ArH-6), 7.08 (2H, d, J=8.8 Hz, ArH-2',6'), 7.24 (2H, s, ArH-3",5"), 7.33 (1H, d, J=16.4 Hz, CH=), 7.50 (2H, d, J=8.8 Hz, ArH-3',5'), 9.30 (1H, s, ArH-3), 9.82 (1H, s, NH); MS m/z (%) 454.3 (M+1, 100).

Example 10

Preparation of 4-carbamoyl-N$^1$-(4'-cyanophenyl)-5-(4"-cyanoethyl-2",6"-dimethylphenoxy)-1,2-phenylenediamine (Compound 10)

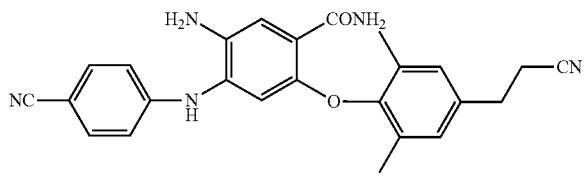

Compound 9 (453 mg, 1 mmol) was subjected to catalytic hydrogenation (Method A in Preparation Example 3) to get Compound 10 (357 mg), with a yield of 84%; off-white solid; m.p. 274-276° C.; $^1$H NMR (CDCl$_3$) δ ppm 2.14 (6H, s, 2×CH$_3$), 2.63 (2H, t, J=7.2 Hz, CH$_2$CN), 2.89 (2H, t, J=7.2 Hz, ArCH$_2$), 5.90 (1H, s, NH), 6.23 (1H, s, ArH-6), 6.70 (2H, d, J=8.8 Hz, ArH-2',6'), 6.99 (2H, s, ArH-3",5"), 7.43 (2H, d, J=8.8 Hz, ArH-3',5'), 7.79 (1H, s, ArH-3), 5.93, 7.85 (—CONH$_2$); MS m/z (%) 426.4 (M+1, 100).

Example 11

Preparation of N$^1$-(4'-cyanophenyl)-5-(4"-cyanovinyl-2",6"-dimethylphenoxy)-4-(N-methylacylamino)-2-nitroaniline (Compound 11)

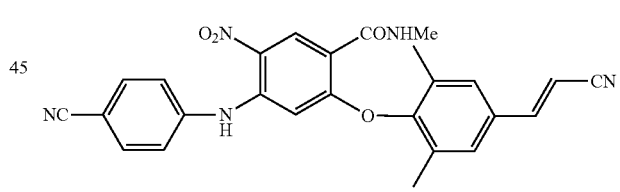

Compound 7 and SOCl$_2$ (0.5 mL) were stirred in anhydrous THF for a moment, aqueous methylamine (25-30%, 1 mL) was added in the condition of an ice bath. The resultant solution was stirred for 30 min, and poured into ice-water to precipitate a solid. The mixture was filtered and isolated through silica gel column chromatography to get Compound 11, with a yield of 60%; yellow solid; m.p. 218-220° C.; $^1$H NMR δ ppm 2.17 (6H, s, 2×CH$_3$), 3.08 (3H, d, CH$_3$), 5.88 (1H, d, J=16.4Hz, =CH), 6.28 (1H, s, ArH-6), 7.07 (2H, d, J=8.8 Hz, ArH-2',6'), 7.25 (2H, s, ArH-3",5"), 7.34 (1H, d, J=16.4Hz, CH=), 7.49 (2H, d, J=8.8 Hz, ArH-2',6'), 7.50 (1H, NMe), 9.29 (1H, s, ArH-3), 9.78 (1H, s, NH); MS m/z (%) 468.3 (M+1, 100).

Example 12

Preparation of 5-(4"-cyanoethyl-2",6"-dimethylphenoxy)-N¹-(4'-cyanophenyl)-4-(N-methyl-carbamoyl)-1,2-phenylenediamine (Compound 12)

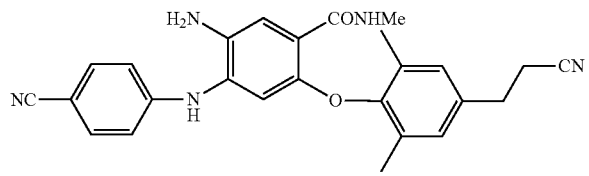

Compound 11 (467 mg, 1 mmol) was subjected to catalytic hydrogenation (Method A in Preparation Example 3) to get Compound 12 (289 mg), with a yield of 66%; off-white solid; m.p. 110-112° C.; $^1$H NMR (CDCl$_3$) δ ppm 2.10 (6H, s, 2×CH$_3$), 2.63 (2H, t, J=7.2 Hz, CH$_2$CN), 2.89 (2H, t, J=7.2 Hz, ArCH$_2$), 3.06 (3H, d, J=4.8 Hz, OCH$_3$), 5.85 (1H, s, NH), 6.21 (1H, s, ArH-6), 6.67 (2H, d, J=8.8 Hz, ArH-2',6'), 6.98 (2H, s, ArH-3",5"), 7.42 (2H, d, J=8.8 Hz, ArH-3',5'), 7.82 (1H, s, ArH-3), 7.97 (1H, d, J=4.8 Hz, CONH); MS m/z (%) 440.4 (M+1, 100).

Example 13

Preparation of N-(4'-cyanophenyl)-5-(4"-cyanovinyl-2",6"-dimethylphenoxy)-4-aminosulfonyl-2-nitroaniline (Compound 13)

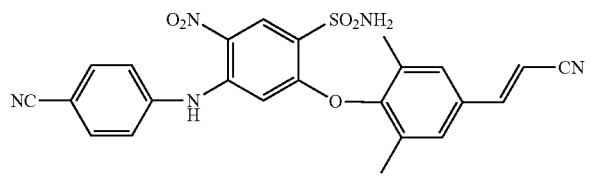 [SMILES: Cc1cc(/C=C/C#N)cc(C)c1Oc1cc(Nc2ccc(C#N)cc2)c([N+](=O)[O-])cc1S(N)(=O)=O]

4-cyano aniline and 2,4-dichloro-5-aminosulfonyl-nitrobenzene as starting materials were coupled by Method A in Preparation Example 1 to get 4-chloro-N²-(4'-cyanophenyl)-5-aminosulfonyl-nitrobenzene (intermediate I-3). I-3 and 2,6-dimethyl-4-formylphenol were coupled by Method A in Preparation Example 2, and were subjected to acrylcyanidation (Method C) to get Compound 13, with a yield of 45%; yellow solid; m.p. 198-200° C.; $^1$H NMR (DMSO-d$_6$) δ ppm 2.16 (6H, s, 2×CH$_3$), 6.38 (1H, d, J=16.4 Hz, =CH), 6.54 (1H, s, ArH-6), 7.32 (2H, s, ArH-3",5"), 7.51 (2H, d, J=8.8 Hz, ArH-2',6'), 7.52 (1H, d, J=16.4 Hz, =CHCN), 7.85 (2H, d, J=8.8 Hz, ArH-3',5'), 8.25 (1H, s, ArH-3), 9.79 (1H, s, NH); MS m/z (%) 488 (M−1, 100).

Example 14

Preparation of 5-(4"-cyanoethyl-2",6"-dimethylphenoxy)-N¹-(4'-cyanophenyl)-4-aminosulfonyl-1,2-phenylenediamine (Compound 14)

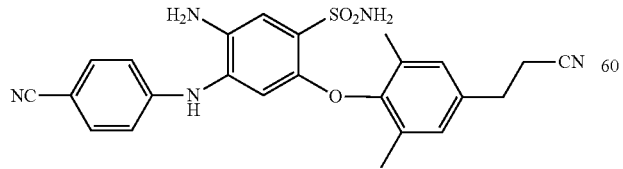

Compound 13 (489 mg, 1 mmol) was subjected to catalytic hydrogenation (Method A in Preparation Example 3) to get Compound 14 (261 mg), with a yield of 57%; off-white solid; m.p. 140-142° C.; $^1$H NMR (CDCl$_3$) δ ppm 2.13 (6H, s, 2×CH$_3$), 2.64 (2H, t, J=6.8 Hz, CH$_2$), 2.86 (2H, t, J=6.8 Hz, ArCH$_2$), 6.14 (1H, s, NH), 6.33 (1H, s, ArH-6), 6.88 (1H, s, ArH-3), 6.93 (2H, s, ArH-3",5"), 7.06 (2H, d, J=8.8 Hz, ArH-2',6'), 7.57 (2H, d, J=8.8 Hz, ArH-3',5'); MS m/z (%) 460.2 (M−1, 100).

Example 15

Preparation of 6-(2,6-dimethyl-4-allyl-phenoxy)-2-(4-cyanoanilinyl)-3-nitropyridine (Compound 15)

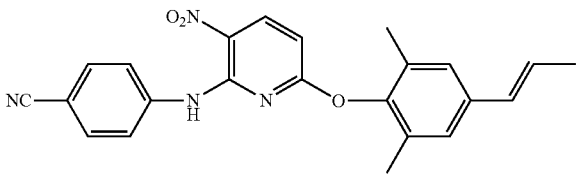 [SMILES: CCCc1cc(C)c(Oc2ccc(N)c(Nc3ccc(C#N)cc3)n2)c(C)c1]

4-cyano aniline was coupled with 2,6-dichloro-3-nitropyridine by Method B in Preparation Example 1 to prepare 6-chloro-N²-(4'-cyanobenzene)-3-nitropyridine (intermediate II-1), which was coupled with 2,6-dimethyl-4-allylphenol by Method B in Preparation 2 to get Compound 15.

Example 16

Preparation of N²-(4-cyanoanilinyl)-6-(2,6-dimethyl-4-propylphenoxy)-3-aminopyridine (Compound 16)

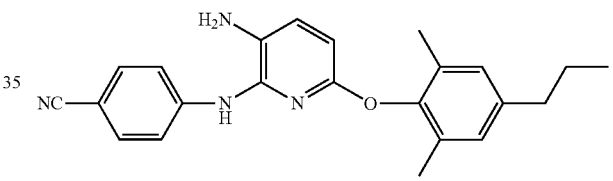

Compound 15 (402 mg, 1 mmol) was subjected to catalytic hydrogenation (Method A in Preparation Example 3) to get Compound 16 (140 mg), with a yield of 38%; gray solid. $^1$H NMR (DMSO-d) δ ppm 0.92 (3H, t, J=7.6 Hz, —CH$_3$), 1.65 (2H, m, CH$_2$), 2.01 (6H, s, ArCH$_3$×2), 2.55 (2H, m, ArCH$_2$), 4.75 (2H, s, NH$_2$), 6.37 (1H, d, J=8.0 Hz, ArH-5), 6.97 (2H, s, ArH-3",5"), 7.11 (1H, d, J=8.0 Hz, ArH-4), 7.29 (2H, d, J=8.8 Hz, ArH-2',6'), 7.38 (2H, d, J=8.8 Hz, ArH-3',5'), 8.30 (1H, s, NH); MS m/z (%) 378 (M+1, 100).

Example 17

Preparation of N-(4'-cyanophenyl)-5-(4"-hydroxymethyl-2",6"-dimethylphenoxy)-4-hydroxymethyl-2-nitroaniline (Compound 17)

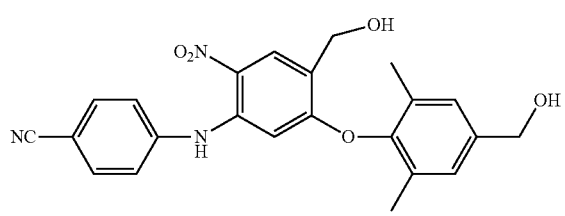 [SMILES: Cc1cc(CO)cc(C)c1Oc1cc(Nc2ccc(C#N)cc2)c([N+](=O)[O-])cc1CO]

Intermediate I-1 and 4''-formyl-2'',6''-dimethylphenol were coupled by Method A in Preparation Example 2, and the product thus obtained was reacted with lithium borohydride in a mixed solvent of THF and methanol, at room temperature under stirring for 1 h, to get the reductant product, i.e. intermediate compound 17, with a yield of 85%; yellow solid; m.p. 216-218° C.; $^1$H NMR δ ppm 2.13 (6H, s, 2×CH$_3$), 4.66 and 4.88 (each 2H, d, CH$_2$O), 6.28 (1H, s, ArH-6), 7.03 (2H, d, J=8.8 Hz, ArH-2',6'), 7.12 (2H, s, ArH-3'',5''), 7.47 (2H, d, J=8.8 Hz, ArH-3',5'), 8.38 (1H, s, ArH-3), 9.70 (1H, s, NH); MS m/z (%) 442.4 (M+Na, 100).

Example 18

Preparation of N$^1$-(4'-cyanophenyl)-5-(4''-hydroxymethyl-2'',6''-dimethylphenoxy)-4-hydroxymethyl-1,2-phenylenediamine (Compound 18)

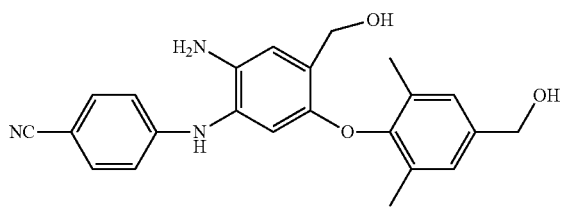 [SMILES: Cc1cc(CO)cc(C)c1Oc1cc(Nc2ccc(C#N)cc2)c(N)cc1CO]

Compound 17 (419 mg, 1 mmol) was subjected to catalytic hydrogenation (Method A in Preparation Example 3) to get Compound 18 (239 mg), with a yield of 62%; off-white solid; $^1$H NMR (CDCl$_3$) δ ppm 2.12 (6H, s, 2×CH$_3$), 3.52 (2H, s, NH$_2$), 4.63 and 4.87 (each 2H, s, ArCH$_2$O), 5.48 (1H, s, NH), 6.06 (1H, s, ArH-6), 6.54 (2H, d, J=8.8 Hz, ArH-2',6'), 6.92 (1H, s, ArH-3), 7.08 (2H, s, ArH-3'',5''), 7.39 (2H, d, J=8.8 Hz, ArH-3',5'); MS m/z (%) 390.3 (M+1, 100).

Example 19

Preparation of N-(4'-cyanophenyl)-5-(4''-cyano-2'',6''-dimethylphenoxy)-4-hydroxymethyl-2-nitroaniline (Compound 19)

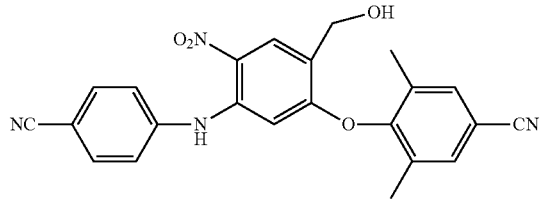 [SMILES: Cc1cc(C#N)cc(C)c1Oc1cc(Nc2ccc(C#N)cc2)c([N+](=O)[O-])cc1CO]

Intermediate I-2 was coupled to 4''-cyano-2'',6''-dimethylphenol by Method A in Preparation Example 2, wherein the ester group on the intermediate ring was reduced with LiBH$_4$ (the method is the same as the one in Example 3) to get Compound 19.

Example 20

Preparation of N$^2$-(4-cyanoanilinyl)-6-(2,6-difluoro-4-cyanovinyl)phenoxy-3-nitropyridine (Compound 20)

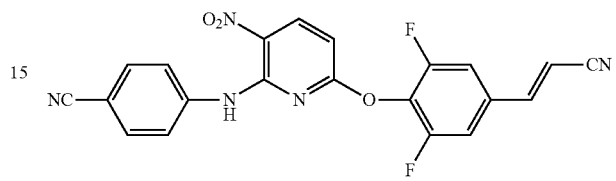

Intermediate II-1 and 2,6-difluoro-4-formylphenol were coupled by Method B in Preparation Example 2, followed by coupling by Method A in Preparation Example 2, and acrylcyanidation (Method C) to get Compound 20.

Example 21

Preparation of N$^2$-(4-cyanoanilinyl)-6-(2,6-difluoro-4-cyanoethyl-phenoxy)-3-aminopyridine (Compound 21)

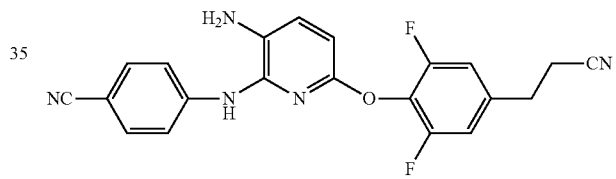

Compound 20 (396 mg, 1 mmol) was subjected to catalytic hydrogenation (Method A in Preparation Example 3) to get Compound 21 (198 mg), with a yield of 52%; gray solid; $^1$H NMR (DMSO-d$_6$) δ ppm: 3.00-2.88 (4H, m, ArCH$_2$CH$_2$CN) 4.91 (2H, s, NH$_2$), 6.55 (1H, d, J=8.4 Hz, ArH-5), 7.15 (1H, d, J=8.4 Hz, ArH-4), 7.35 (2H, d, J=8.8 Hz, ArH-2',6'), 7.39 (2H, d, J=8.4 Hz, ArH-3'',5''), 7.40 (2H, d, J=8.8 Hz, ArH-3',5'), 8.39 (1H, s, NH); MS m/z (%) 390 (M−1, 100).

Example 22

Preparation of 6-(2,6-difluoro-4-methyl acrylate) phenoxy-2-(4-cyanoanilinyl)-3-nitropyridine (Compound 22)

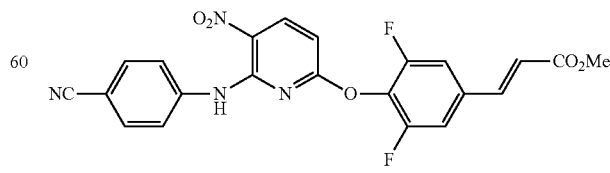

Intermediate II-1 and 2,6-difluoro-4-formylphenol were coupled by Method A in Preparation Example 2; the product and Ph₃PCHCOOMe were refluxed in chloroform overnight under the protection of nitrogen gas. The reaction solution was concentrated and was purified by column chromatography to get Compound 22.

Example 23

Preparation of N²-(4-cyanoanilinyl)-6-(2,6-difluoro-4-methyl propionate phenoxy)-3-aminopyridine (Compound 23)

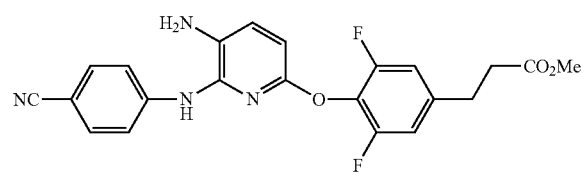 [SMILES: COC(=O)CCc1cc(F)c(Oc2ccc(N)c(Nc3ccc(C#N)cc3)n2)c(F)c1]

Compound 22 (452 mg, 1 mmol) was subjected to catalytic hydrogenation (Method A in Preparation Example 3) to get Compound 23 (158 mg), with a yield of 40%; gray solid; m.p. 209-211° C.; ¹H NMR (DMSO-d₆) δ ppm: 2.72 (2H, t, J=7.6 Hz, CH₂CO), 2.93 (2H, t, J=7.6 Hz, ArCH₂), 3.60 (3H, s, OCH₃), 4.90 (2H, s, NH₂), 6.54 (1H, d, J=8.4 Hz, ArH-5), 7.15 (1H, d, J=8.4 Hz, ArH-4), 7.21 (2H, d, J=9.2 Hz, ArH-3",5"), 7.39-7.34 (4H, m, ArH-2',3',5',6'), 8.39 (1H, s, NH); MS m/z (%) 423 (M−1, 100).

Example 24

Preparation of N²-(4-cyanoanilinyl)-6-(2,6-difluoro-4-(3-hydroxypropyl)phenoxy)-3-aminopyridine (Compound 24)

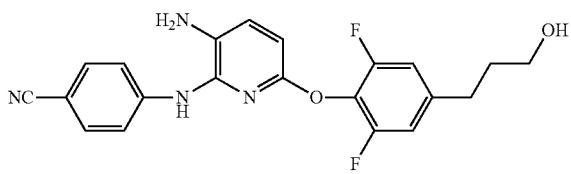 [SMILES: N#Cc1ccc(Nc2nc(Oc3c(F)cc(CCCO)cc3F)ccc2N)cc1]

Compound 22 (452 mg, 1 mmol) was dissolved in the mixture of 15 mL of THF and 15 mL of ethanol, an excessive amount of Pd/C (10%) was added, and the resultant mixture was subjected to catalytic hydrogenation (Method A in Preparation Example 3) at a pressure of 15 Psi for 6 h. Pd/C solid was filtered out, the filtrate was cooled in an ice-water bath, and 280 mg (10 mmol) of LiBH₄ was added in batches. After stirring for 30 min, the reaction finished. The reaction solution was poured into 50 mL of ice-water, the pH was adjusted to 4-5 with 1 mol/L HCl, and the reaction solution was extracted with ethyl acetate, and dried with anhydrous sodium sulfate. After removing the solvent, the residue was isolated by column chromatography to get Compound 24 (264 mg), with a yield of 67%; gray solid; ¹H NMR (DMSO-d₆) δ ppm: 1.76 (2H, m, CH₂), 2.70 (2H, t, J=2.8 Hz, CH₂O), 3.43 (2H, t, J=2.0 Hz, ArCH₂), 4.52 (1H, br s, OH), 4.90 (2H, br s, NH₂), 6.54 (1H, d, J=8.4 Hz, ArH-5), 7.15 (3H, d, J=8.4 Hz, ArH-4,3",5"), 7.36 (4H, s, ArH-2',3',5',6'), 8.40 (1H, s, NH); MS m/z (%) 395 (M−1, 100).

Example 25

Preparation of 6-(2-bromo-((E)-4-cyanovinyl)-5-methoxyphenoxy)-2-(4-cyanoanilinyl)-3-nitropyridine (Compound 25)

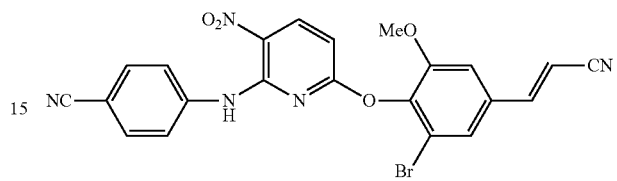

Intermediate II-1 and 2-bromo-6-methoxy-4-formylphenol were coupled by Method A in Preparation Example 2, the product thus obtained was reacted with (EtO)₂P(O)CH₂CN by Method C in Preparation Example 2 to get Compound 25.

Example 26

Preparation of 6-(2-bromo-4-cyanoethyl-5-methoxy)phenoxy-2-(4-cyanoanilinyl)-3-aminopyridine (Compound 26A) and 6-(2-bromo-4-cyanovinyl-5-methoxy)phenoxy-2-(4-cyanoanilinyl)-3-aminopyridine (Compound 26B)

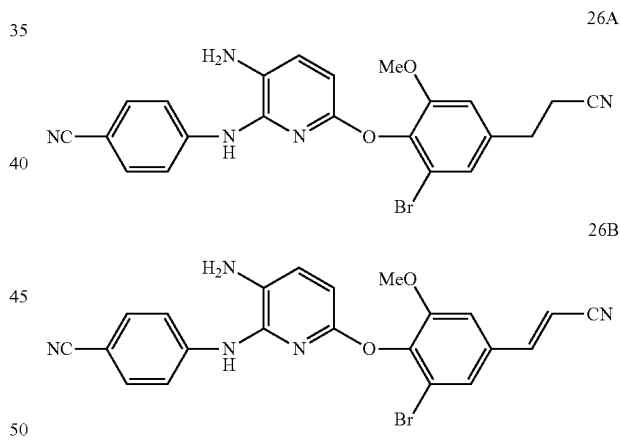

Compound 25 (492 mg) was reduced by catalytic hydrogenation (Method A in Preparation Example 3), under stirring at room temperature for 2 h. After conventional post-treatment and isolation by column chromatography, Compound 26A (285 mg) was obtained with a yield of 61%; gray solid; m.p. 242-244° C.; ¹H-NMR δ ppm 8.35 (1H, s, NH), 7.69 (1H, d, J=16.4 Hz, ArH—CH=CH), 7.65 (1H, s, ArH-5"), 7.55 (1H, s, ArH-3"), 7.31 (4H, s, ArH-2',3',5',6'), 7.13 (1H, d, J=8.0 Hz, ArH-4), 6.68 (1H, d, J=8.0 Hz, ArH-5), 4.83 (2H, s, NH₂), 3.75 (3H, s, ArOCH₃), 3.00-2.88 (4H, m, ArCH₂CH₂CN); MS m/z 462 [M−1, 100].

Compound 25 (492 mg) was selectively reduced with sodium hydrosulfite (Method B in Preparation Example 3) to get 285 mg of Compound 26B, with a yield of 61%; white solid; 219-220° C.; ¹H NMR δ ppm 8.35 (1H, s, NH), 7.69 (1H, d, J=16.4 Hz, ArCH=), 7.65 (1H, s, ArH-3"), 7.55 (1H, s, ArH-5"), 7.31 (4H, br s, ArH-2',3',5',6'), 7.13 (1H, d, J=8.8 Hz, PyH-4), 6.68 (1H, d, J=16.4 Hz, =CHCN), 6.48 (1H, d, J=8.8 Hz, PyH-5), 4.83 (2H, s, NH$_2$), 3.75 (3H, s, OCH$_3$); MS m/z (%) 460.3 (M−1, 100), 462.1 (M+1, 60).

Example 27

Preparation of 3-nitro-6-(2,6-dibromo-4-((E)-cyanovinyl)phenoxy)-2-(4-cyanoanilinyl)pyridine (Compound 27)

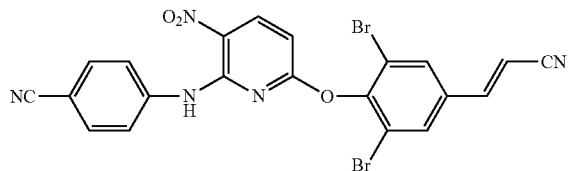 [SMILES: N#C/C=C/c1cc(Br)c(Oc2ccc([N+](=O)[O-])c(Nc3ccc(C#N)cc3)n2)c(Br)c1]

Intermediate II-1 and 2,6-dibromo-4-formylphenol were coupled by method in Preparation Example 2, and the product was subjected to acrylcyanidation according to Method C in Preparation Example 2 to get Compound 27.

Example 28

Preparation of 2-(4-cyanoanilinyl)-6-(2,6-dibromo-4-cyanoethyl)phenoxy)-3-aminopyridine (Compound 28)

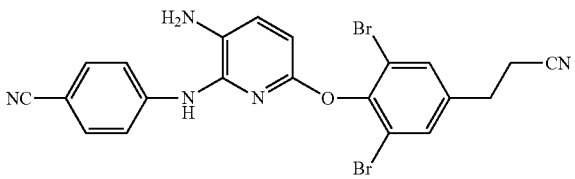 [SMILES: N#CCCc1cc(Br)c(Oc2ccc(N)c(Nc3ccc(C#N)cc3)n2)c(Br)c1]

Compound 27 (541 mg) was subjected to catalytic hydrogenation reduction (Method A in Preparation Example 3) to get Compound 28 (200 mg), with a yield of 43%; gray solid; m.p. 231-233° C.; $^1$H NMR δ ppm: 8.39 (1H, s, NH), 8.15 (2H, s, ArH-3",5"), 7.31-7.29 (4H, m, ArH-2',3',5',6'), 7.16 (1H, d, J=8.0 Hz, ArH-4), 6.56 (1H, d, J=8.0 Hz, ArH-5), 4.90 (2H, s, NH$_2$), 3.00-2.88 (4H, m, ArCH$_2$CH$_2$CN); MS m/z 512 [M−1, 100].

Example 29

Preparation of N$^2$-(4-cyanoanilinyl)-6-(2,6-difluoro-4-((E)-1-methyleneacetonyl)phenoxy)-3-nitropyridine (Compound 29)

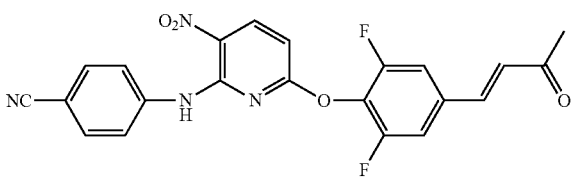 [SMILES: CC(=O)/C=C/c1cc(F)c(Oc2ccc([N+](=O)[O-])c(Nc3ccc(C#N)cc3)n2)c(F)c1]

Intermediate II-1 and 2,6-difluoro-4-formylphenol were coupled by Method A in Preparation Example 2; the resultant product and acetone were stirred in aqueous NaOH solution (10%, 2 mL) at room temperature for 1 h, and were poured into water. The pH was adjusted to be acidic to precipitate a solid. The mixture was filtered, washed, dried, and isolated by flash preparative chromatography to get Compound 29; yellow solid; m.p. 275-277° C.

Example 30

Preparation of N$^2$-(4-cyanoanilinyl)-6-(2,6-difluoro-4-(2-butanonyl)phenoxy)-3-aminopyridine (Compound 30)

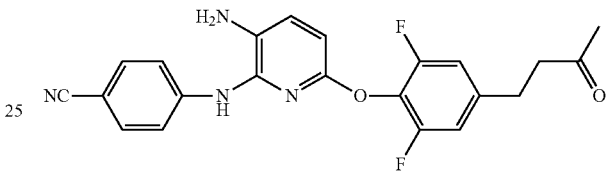

Compound 29 (436 mg) was subjected to catalytic hydrogenation (Method A in Preparation Example 3) to get Compound 30 as the reduction product (167 mg), with a yield of 43%; grey solid; m.p. 142-144° C., $^1$H NMR δ ppm: 8.42 (1H, s, NH), 7.40 (2H, d, J=8.8 Hz, ArH-3',5'), 7.35 (2H, d, J=8.8 Hz, ArH-2',6'), 7.19-7.14 (3H, m, ArH-4, 3",5"), 6.55 (1H, d, J=8.0 Hz, ArH-5), 4.92 (2H, s, NH$_2$), 2.87-2.81 (4H, m, ArCH$_2$CH$_2$CO), 2.14 (3H, s, ArCH$_2$CH$_2$COCH$_3$); MS m/z 407 [M−1, 100].

Example 31

Preparation of N-(4'-cyanophenyl)-5-(4"-cyano-2", 6"-dimethylphenoxy)-4-chloromethyl-2-nitroaniline (Compound 31)

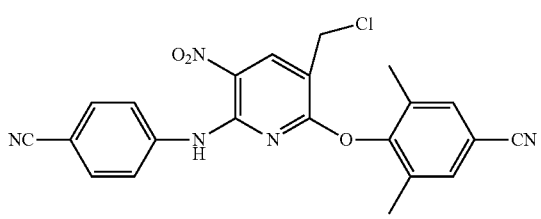 [SMILES: Cc1cc(C#N)cc(C)c1Oc1nc(Nc2ccc(C#N)cc2)c([N+](=O)[O-])cc1CCl]

Dichloromethane solution of Compound 19 was added dropwise at room temperature to DMF solution of cyanuric chloride, and the temperature was increased to 70-80° C. After stirring for about 1-2 h, the resultant solution was poured into ice-water, extracted with ethyl acetate, dried, filtered, concentrated, isolated and purified to get Compound 31.

Example 32

Preparation of N-(4'-cyanophenyl)-5-(4"-cyanovinyl-2",6"-dimethylphenoxy)-4-[(2-methoxyethoxyl)methyl]-2-nitroaniline (Compound 32)

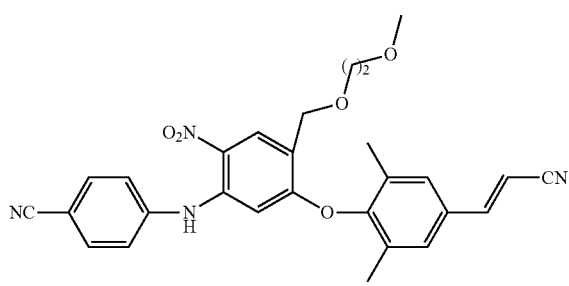

Compound 5 (105 mg, 0.24 mmol), 2-methoxy bromoethane (50 mg, 0.36 mmol), $K_2CO_3$ (104 mg, 0.75 mmol) and DMF (5 mL) were added to a 3-neck flask in an oil bath and heated at 70° C. for 6 h until the reaction finished. The reaction solution was poured into ice-water, the pH was adjusted to neutral, and a yellow solid was precipitated. After standing, filtration, and drying, the residue was isolated through PTLC ($CH_2Cl_2$:$CH_3OH$ 200:1) to get a tawny solid (52 mg), with a yield of 44%. $^1$H NMR δ ppm 8.29 (1H, s, ArH-3), 7.38 (2H, d, J=8.0 Hz, ArH-3',5'), 7.33 (2H, d, J=16.0 Hz, CH=), 7.23 (2H, s, ArH-3",5"), 6.48 (1H, s, ArH-6), 6.44 (2H, d, J=8.0 Hz, ArH-2',6'), 5.84 (1H, d, J=16.0 Hz, =CH), 5.02 (2H, d, J=4.0 Hz, $CH_2O$), 3.75 (2H, t, J=8.0 Hz, $OCH_2CH_2O$), 3.45 (2H, t, J=12.0 Hz, $OCH_2CH_2O$), 3.02 (3H, s, $OCH_3$), 2.15 (6H, s, 2×$CH_3$); MS m/z 499 (M+1).

Example 33

Preparation of $N^1$-(4'-cyanophenyl)-5-(4"-cyanovinyl-2",6"-dimethylphenoxy)-4-(2-methoxyethoxyl)methyl-1,2-phenylenediamine (Compound 33)

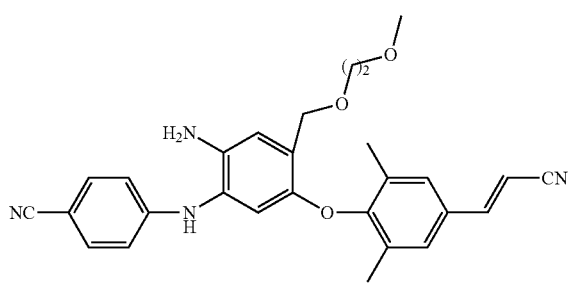

Compound 32 was reduced with $Na_2S_2O_4$ (Method B in Preparation Example 3) to get Compound 33, with a yield of 22%, as a white solid. $^1$HNMR δ ppm 2.13 (6H, s, 2×$CH_3$), 3.21 (3H, s, $OCH_3$), 3.46 (2H, t, J=7.0 Hz, $CH_2O$), 3.68 (4H, s, $OCH_2$, $NH_2$), 4.88 (2H, s, $CH_2$), 5.79 (1H, d, J=16.4 Hz, =CH), 5.98 (1H, s, ArH-6), 6.51 (2H, d, J=8.8 Hz, ArH-2',6'), 6.95 (1H, s, ArH-3), 7.17 (2H, s, ArH-3",5"), 7.30 (1H, d, J=16.8 Hz, CH=), 7.37 (2H, d, J=7.2 Hz, ArH-3',5'); MS m/z (%) 483.4 (M+1, 47), (M+Na, 100).

Example 34

Preparation of 5-(4"-cyanoethyl-2",6"-dimethylphenoxy)-$N^1$-(4'-cyanophenyl)-4-(2-cyclopropylaminomethyl)-1,2-phenylenediamine (Compound 34)

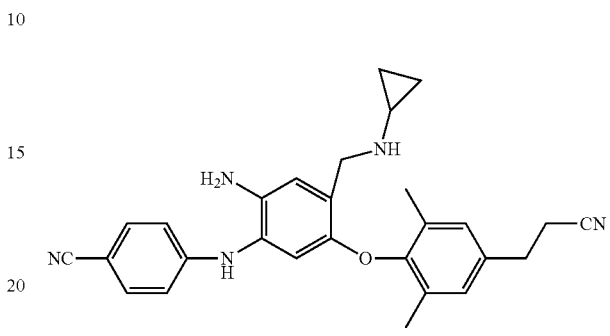

By reference to the method in Example 31, Compound 5 (1 g, 2.27 mmol) and cyanuric chloride (627 mg, 3.41 mmol) were used to prepare the corresponding chloro compound (800 mg), with a yield of 77%. The chloride (200 mg, 0.44 mmol) was dissolved in acetonitrile, cyclopropylamine (3 drops) was added in the condition of ice bath, and the reaction was carried out at room temperature. After the reaction finished as monitored by TLC, the corresponding nitro compound (130 mg) was isolated with a yield of 62%. The nitro compound (110 mg, 0.23 mmol) was subjected to catalytic hydrogenation (Method A in Preparation Example 3) in ethanol to get Compound 34 (60 mg), with a yield of 58%, as a white solid. $^1$HNMR δ ppm 0.48 (4H, m, $CH_2CH_2$), 2.10 (6H, s, 2×$CH_3$), 2.23 (1H, m, CH), 2.14 (2H, t, J=7.0 Hz, $CH_2CN$), 2.88 (2H, t, J=7.0 Hz, $ArCH_2$), 3.53 (2H, s, $NH_2$), 3.99 (2H, s, $ArCH_2$), 5.51 (1H, s, NH), 6.02 (1H, s, ArH-6), 6.54 (2H, d, J=8.8 Hz, ArH-2',6'), 6.86 (1H, s, ArH-3), 6.94 (2H, s, ArH-3",5"), 7.40 (2H, d, J=9.2 Hz, ArH-3',5'); MS m/z (%) 354.1 (M−98, 100), 474.0 (M+Na, 10).

Example 35

Preparation of 5-(4"-cyanoethyl-2",6"-dimethylphenoxy)-$N^1$-(4'-cyanophenyl)-4-amino-1,2,4-triaminobenzene (Compound 35)

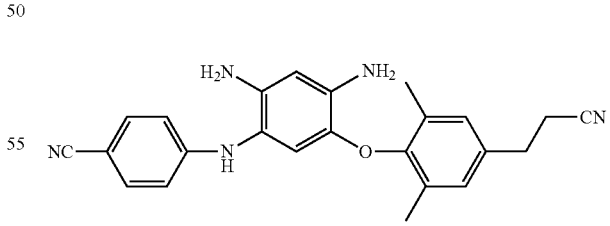

Compound 5-(4"-cyanovinyl-2",6"-dimethylphenoxy)-$N^1$-(4'-cyanophenyl)-2,4-dinitroaniline (please refer to *J. Med. Chem.* 2010, 51, 8287-8296 for the preparation method thereof) was subjected to catalytic hydrogenation (Method A in Preparation Example 3) to get Compound 40, with a yield of 70%; white solid; m.p. 118-20° C., $^1$H NMR δ ppm 2.11 (6H, s, 2×$CH_3$), 2.61 (2H, t, J=7.2 Hz, $CH_2CN$), 2.86 (2H, t, J=7.2 Hz, $CH_2Ar$), 5.36 (1H, s, NH), 5.94 (1H, s, ArH-6), 6.30

(1H, s, ArH-3), 6.48 (2H, d, J=8.8 Hz, ArH-2',6'), 6.91 (2H, s, ArH-3",5"), 7.37 (2H, d, J=8.8 Hz, ArH-3',5'); MS m/z (%) 398 (M+1, 100).

Example 36

Preparation of 5-(4"-cyanoethyl-2",6"-dimethylphenoxy)-N$^1$-(4'-cyanophenyl)-4-formhydrazide-1,2-phenylenediamine (Compound 36)

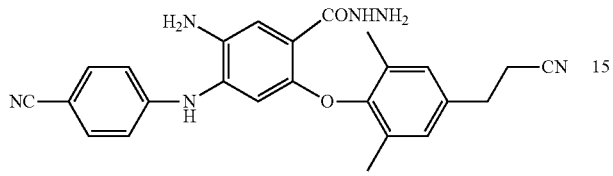

Compound 7 (140 mg, 0.30 mmol) was reacted with SOCl$_2$ (0.50 mL) and then dissolved in dried THF (3 mL), and aqueous hydrazine hydrate solution (85%, 1 mL) was slowly added dropwise at room temperature, under stirring for 1 h. The crude product obtained by post-treatment was isolated through silica gel column chromatography (MeOH/CH$_2$Cl$_2$) to get 116 mg of diarylnitrobenzene compound, which was subjected to catalytic hydrogenation (Method A in Preparation Example 3) to get Compound 36, with a yield of 75%, as a white solid; $^1$H NMR δ ppm 2.11 (6H, s, 2×CH$_3$), 2.61 (2H, t, J=6.8 Hz, CH$_2$CN), 2.86 (2H, t, J=6.8 Hz, CH$_2$Ar), 6.21 (1H, s, ArH-6), 6.30 (1H, s, NH), 6.48 (2H, d, J=8.8 Hz, ArH-2',6'), 6.98 (2H, s, ArH-3",5"), 7.00 (1H, s, ArH-3), 7.43 (1H, d, J=8.8 Hz, ArH-3',5'); MS m/z (%) 441 (M+1, 100).

Example 37

Preparation of 4-acetyloxymethyl-N$^1$-(4'-cyanophenyl)-5-(4"-cyanoethyl-2",6"-dimethylphenoxy)-1,2-phenylenediamine (Compound 37)

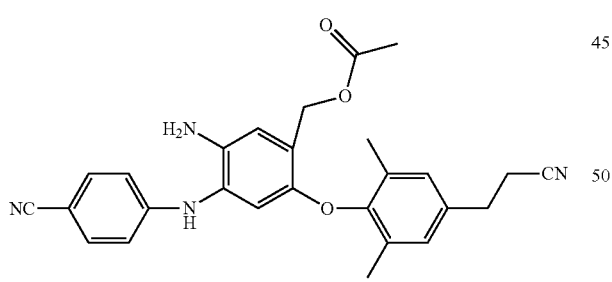

Compound 5 (93 mg, 0.21 mmol), sodium hydroxide (30 mg, 0.75 mmol) and 3 ml of acetic acid were placed in a microwave tube, and heated by microwave at 100° C. for 5 min. The reaction solution was poured into a suitable amount of ice-water, and stirred at room temperature, and yellow solid was precipitated. Sucking filtration was performed to get the ester compound (93 mg, yellow solid), with a yield of 95%. The compound (80 mg, 0.17 mmol) was subjected to catalytic hydrogenation (Method A in Preparation Example 3) in ethanol to get 30 mg of Compound 37, with a yield of 40.0% as a white solid. $^1$HNMR (DMSO-d$_6$) δ ppm 2.04 (6H, s, 2×CH$_3$), 2.09 (3H, s, COCH$_3$), 2.78 (4H, s, ArCH$_2$CH$_2$CN), 4.58 (2H, s, NH$_2$), 5.19 (2H, s, CH$_2$O), 5.90 (1H, s, NH), 6.54 (2H, d, J=9.2 Hz, ArH-2',6'), 6.87 (1H, s, ArH-6), 7.04 (2H, s, ArH-3",5"), 7.45 (2H, d, J=8.8 Hz, ArH-3',5'), 8.08 (1H, s, ArH-3); MS m/z (%) 395.2 (M−59, 100), 455.3 (M+1, 17).

Example 38

Preparation of N$^1$-(4'-cyanophenyl)-5-(4"-cyanoethyl-2",6"-dimethylphenoxy)-4-methoxymethyl-1,2-phenylenediamine (Compound 38)

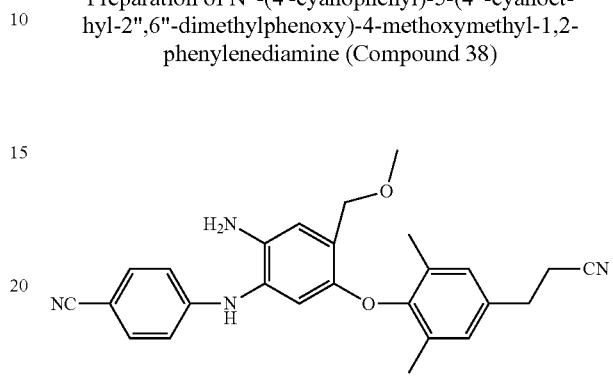

Compound 5 (110 mg, 0.25 mmol) was dissolved in dichloromethane, and then was added to a mixture of CCl$_4$, bismuth chloride (98 mg, 0.31 mmol) and methanol. After stirring at room temperature for 2-6 h, undissolved substance was filtered out, and the organic phase was dried over anhydrous sodium sulfate, and isolated and purified to get 80 mg methyl ether nitro compound, with a yield of 61%, as a yellow solid. The nitro compound (150 mg, 0.33 mmol) was subjected to catalytic hydrogenation (Method A in Preparation Example 3) in ethanol to prepare Compound 38 (110 mg), with a yield of 79%, % as a white solid. $^1$HNMR (CDCl$_3$) δ ppm 2.09 (6H, s, 2×CH$_3$), 2.61 (2H, t, J=7.2 Hz, CH$_2$CN), 2.87 (2H, t, J=7.2 Hz, ArCH$_2$), 3.52 (3H, s, OCH$_3$), 4.67 (2H, s, CH$_2$O), 5.56 (1H, s, NH), 6.03 (1H, s, ArH-6), 6.55 (2H, d, J=8.8 Hz, ArH-2',6'), 6.92 (2H, s, ArH-3",5"), 6.99 (1H, s, ArH-3), 7.39 (2H, d, J=8.8 Hz, ArH-3',5'); MS m/z (%) 427.3 (M+1, 100).

Example 39

Preparation of N$^1$-(4'-cyanophenyl)-5-(4"-cyanoethyl-2",6"-dimethylphenoxy)-4-cyclopropionyloxymethyl-1,2-phenylenediamine (Compound 39)

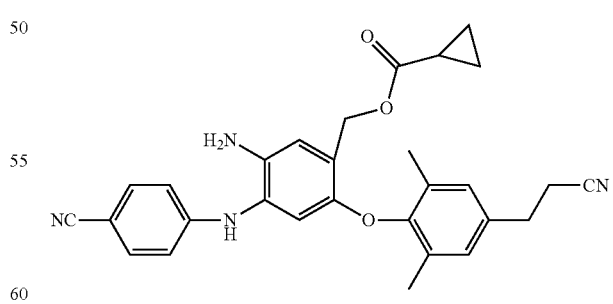

Compound 5 (80 mg, 0.18 mmol) was dissolved in dichloromethane, and cyclopropionylchloride (28.6 mg, 0.27 mmol) and pyridine (1 ml) were added. After stirring at room temperature for 4 h, the reaction finished. The resultant solution was washed with 5% hydrochloric acid, washed with water, dried with anhydrous sodium sulfate, concentrated under reduced pressure, and isolated through preparative silica gel plate or column to get 74 mg of nitro compound (yellow solid), with a yield of 89%. The nitro compound (180 mg) was subjected to catalytic hydrogenation (Method A in Preparation Example 3) to get 35 mg of Compound 29, with a yield of 21%, as a white solid. $^1$HNMR δ ppm 0.90 (2H, m, CH$_2$), 1.06 (2H, m, CH$_2$), 1.70 (1H, m, CH), 2.10 (6H, s, 2×CH$_3$), 2.61 (2H, t, J=6.8 Hz, CH$_2$CN), 2.87 (2H, t, J=7.4 Hz, ArCH$_2$), 3.48 (2H, s, NH$_2$), 5.31 (2H, s, CH$_2$O), 5.56 (1H, s, NH), 6.06 (1H, s, ArH-6), 6.58 (2H, d, J=8.8 Hz, ArH-2',6'), 6.92 (3H, s, ArH-3",5"), 7.41 (2H, d, J=8.8 Hz, ArH-3',5').

Example 40

Preparation of N$^1$-(4'-cyanophenyl)-5-(4"-cyanoethyl-2",6"-dimethylphenoxy)-4-[N,N-dimethylaminomethyl]-1,2-phenylenediamine (Compound 40)

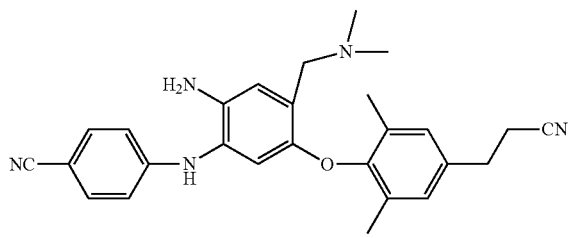 [SMILES: Cc1cc(CCC#N)cc(C)c1Oc1cc(Nc2ccc(C#N)cc2)c(N)cc1CN(C)C]

Compound 5 (1 g, 2.27 mmol) and cyanuric chloride (627 mg, 3.41 mmol) were used to prepare the corresponding chloro compound (800 mg) by reference to the method of Example 31, with a yield of 77%. The chloride (200 mg, 0.44 mmol) was then dissolved in acetonitrile, and aqueous dimethylamine solution (33%, 5 drops) was added in the condition of ice bath. After the reaction (under the conditions that were the same as those in Example 34) finished, the corresponding nitro compound (110 mg) was obtained by isolation, with a yield of 54%. The nitro compound (100 mg, 0.21 mmol) was subjected to catalytic hydrogenation in ethyl acetate (Method A in Preparation Example 3) to get 70 mg of Compound 40, with a yield of 74%, as a light yellow solid. $^1$HNMR δ ppm 2.08 (6H, s, 2×CH$_3$), 2.39 (6H, s, 2×CH$_3$), 2.61 (2H, t, J=7.2 Hz, CH$_2$CN), 2.87 (2H, t, J=7.2 Hz, ArCH$_2$), 3.67 (2H, s, ArCH$_2$), 5.51 (1H, s, NH), 6.02 (1H, s, ArH-6), 6.54 (2H, d, J=8.8 Hz, ArH-2',6'), 6.94 (2H, s, ArH-3",5"), 7.01 (1H, s, ArH-3), 7.40 (2H, d, J=9.2 Hz, ArH-3',5'); MS m/z (%) 395.2 (M−45, 100).

Example 41

Preparation of N$^1$-(4'-cyanophenyl)-5-(4"-cyanoethyl-2",6"-dimethylphenoxy)-4-[N-ethylformamido]-1,2-phenylenediamine (Compound 41)

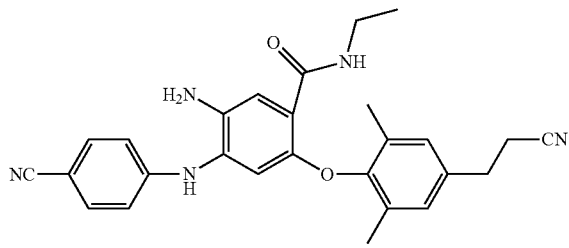 [SMILES: CCNC(=O)c1cc(N)c(Nc2ccc(C#N)cc2)cc1Oc1c(C)cc(CCC#N)cc1C]

Compound 7 (300 mg, 0.66 mmol) was dissolved in thionyl chloride (10 mL) and was cooled to room temperature after reflux for 4 h, the reaction solution was poured into petroleum ether, standed for 10 min, and filtered to get a yellow solid. The solid was dissolved in THF (10 mL), and was cooled to 0° C. Aqueous ethylamine solution (3 drops, 65-75%) was added, and stirred at room temperature for 1 h. The reaction solution was washed with water, dried over anhydrous sodium sulfate, and concentrated under reduced pressure. The crude product was purified through column chromatography to get 130 mg of yellow solid, with a yield of 41%. The nitro compound (120 mg, 0.25 mmol) was subjected to catalytic hydrogenation in ethyl acetate (Method A in Preparation Example 3) to get 68 mg of Compound 41, with a yield of 60%, as a white solid. $^1$H NMR δ ppm 1.24 (3H, t, J=7.2 Hz, CH$_3$), 2.13 (6H, s, 2×CH$_3$), 2.60 (2H, t, J=7.2 Hz, CH$_2$CN), 2.89 (2H, t, J=7.0 Hz, ArCH$_2$), 3.55 (2H, m, J=7.2 Hz, J=5.6 Hz, NHCH$_2$), 5.88 (1H, s, NH), 6.21 (1H, s, ArH-6), 6.70 (2H, d, J=8.8 Hz, ArH-2',6'), 6.84 (1H, s, ArH-3), 7.00 (2H, s, ArH-3",5"), 7.41 (2H, d, J=9.2 Hz, ArH-3',5'), 7.82 (1H, s, ArH-3), 7.98 (1H, t, J=5.6 Hz, CONH); MS m/z (%) 454.4 (M+1, 100).

Example 42

Preparation of N$^1$-(4'-cyanophenyl)-5-(4"-cyanoethyl-2",6"-dimethylphenoxy)-4-[N,N-dimethylformamido]-1,2-phenylenediamine (Compound 42)

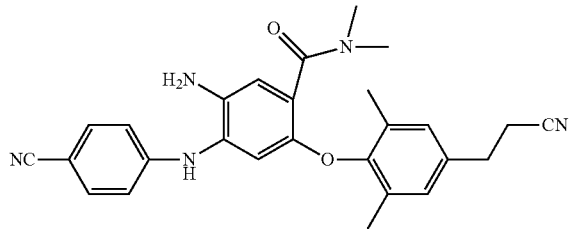 [SMILES: Cc1cc(CCC#N)cc(C)c1Oc1cc(Nc2ccc(C#N)cc2)c(N)cc1C(=O)N(C)C]

The preparation method was the same as the one in Example 41. Compound 7 (300 mg, 0.66 mmol) was subjected to chloroformylation reaction, and was subjected to amidation with aqueous dimethylamine solution (5 drops, 33%) to get the corresponding nitro compound (249 mg), with a yield of 79%, as a yellow solid. The nitro compound (227 mg, 0.47 mmol) was subjected to catalytic hydrogenation in ethyl acetate (Method A in Preparation Example 3, 24 h) to get 156 mg of Compound 42, with a yield of 78%, as a white solid. $^1$H NMR (CDCl$_3$) δ ppm 2.10 (6H, s, 2×CH$_3$), 2.60 (2H, t, J=7.2 Hz, CH$_2$CN), 2.86 (2H, t, J=7.2 Hz, ArCH$_2$), 3.10 (3H, s, CH$_3$), 3.16 (3H, s, CH$_3$), 3.60 (2H, s, NH$_2$), 5.77 (1H, s, NH), 6.12 (1H, s, ArH-6), 6.60 (2H, d, J=8.8 Hz, ArH-2',6'), 6.84 (1H, s, ArH-3), 6.92 (2H, s, ArH-3",5"), 7.39 (2H, d, J=9.2 Hz, ArH-3',5'); MS m/z (%) 454 (M+1, 100).

Example 43

Preparation of N[1]-(4'-cyanophenyl)-5-(4''-cyanoethyl-2'',6''-dimethylphenoxy)-4-[N-cyclopropylformamido]-1,2-phenylenediamine (Compound 43)

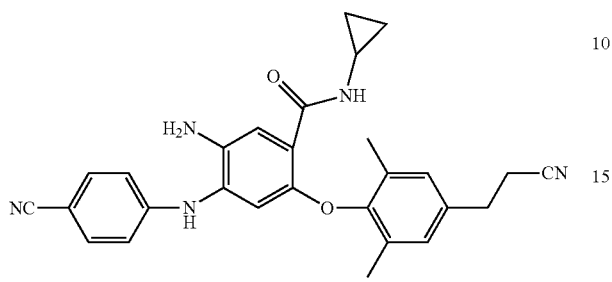

The preparation method was the same as the one in Example 41. Compound 7 (250 mg, 0.55 mmol) was subjected to chloroformylation reaction, and then was subjected to amidation with cyclopropylamine (0.1 mL) to get the corresponding nitro compound (170 mg), with a yield of 63%, as a yellow solid. The nitro compound (150 mg, 0.3 mmol), was subjected to catalytic hydrogenation in ethyl acetate (Method A in Preparation Example 3, about 7 h) to get Compound 43 (115 mg), with a yield of 82%, as a white solid. $^1$H NMR (CDCl$_3$) δ ppm 1.42 (4H, 2×CH$_2$), 2.08 (6H, s, 2×CH$_3$), 2.17 (1H, m, CH), 2.60 (2H, t, J=7.2 Hz, CH$_2$CN), 2.86 (2H, t, J=7.2 Hz, ArCH$_2$), 4.66 (2H, br, NH$_2$), 5.53 (1H, br, NH), 6.02 (1H, s, ArH-6), 6.54 (2H, d, J=8.8 Hz, ArH-2',6'), 6.91 (2H, s, ArH-3'',5''), 6.97 (1H, s, ArH-3), 7.39 (2H, d, J=8.8 Hz, ArH-3',5'); MS m/z (%) 466 (M+1, 100).

Example 44

Anti-HIV Activity Assay (TZM-bl Cell Model)

The assay was carried out by reference to the document (Dang, Z, et al. J. Med. Chem. 2009, 52, 7887-7891). In particular, in a 96-well cell culture plate, solutions of the compounds to be tested at different concentrations were mixed with TZM-bl cells (from National Institutes of Health (NIH)) infected with 200 TCID50 NL4-3 virus, respectively. 2 days later, the culture medium was removed, 100 µl of Bright Glo reagent was added to each well, and Victor 2 luminometer was used to detect the fluorescence of the cells. CalcuSyn software was used to calculate the 50% effective concentration (EC$_{50}$) of the compounds. The results are shown in Table 2.

TABLE 2

Anti-HIV activity of some compounds of formula I according to the invention (NL4-3HIV-wild)

| Compound | EC$_{50}$ (µM)$^a$ | CC$_{50}$ (µM)$^b$ | SI$^c$ |
|---|---|---|---|
| 2 | 0.00113 | >7.1 | >6,283 |
| 4 | 0.0043 | >22.7 | >5255 |
| 6 | 0.00039 | >23.8 | 61026 |
| 10 | 0.00139 | >9.4 | >6762 |
| 12 | 0.00273 | >9.1 | >3330 |
| 16 | 0.0147 | 16.4 | 1116 |
| 18 | 0.0100 | >15.9 | >1590 |
| 21 | 0.0028 | >10.2 | >3643 |

TABLE 2-continued

Anti-HIV activity of some compounds of formula I according to the invention (NL4-3HIV-wild)

| Compound | EC$_{50}$ (µM)$^a$ | CC$_{50}$ (µM)$^b$ | SI$^c$ |
|---|---|---|---|
| 23 | 0.099 | >15.3 | >155 |
| 24 | 0.048 | >25.2 | >525 |
| 26A | 0.00325 | 21 | 6563 |
| 26B | 0.0257 | 21.3 | 1207 |
| 28 | 0.00033 | 8.21 | 24878 |
| 30 | 0.0047 | >9.8 | >2130 |
| 33 | 0.0213 | >5 | >235 |
| 34 | 0.00053 | >5 | >9434 |
| 35 | 0.0061 | >5 | >820 |
| 36 | 0.0191 | >22.7 | >1188 |
| 37 | 0.00329 | >5 | >1520 |
| 38 | 0.00218 | >5 | >2293 |
| 39 | 0.00163 | >5 | >3067 |
| 40 | 0.00273 | >5 | >1832 |
| 41 | 0.00463 | >5 | >1080 |
| 42 | 0.00617 | >5 | >810 |
| 43 | 0.00133 | >5 | >3760 |

$^a$a concentration effective to inhibit the replication of half of viruses, which represents the anti-viral activity of a compound;
$^b$a concentration effective to inhibit the growth of half of cells, which represents the cytotoxicity of a compound;
$^c$selective index of a compound, which is a ratio of toxic CC$_{50}$ value to active EC$_{50}$ value;

TABLE 3

Activity against drug-resistant viruses and drug-like properties of some high active compounds

| Compound | Drug-resistant viruses EC$_{50}$ (nM) | | | Water-solubility$^g$ µg/mL | HLM$^h$ t$_{1/2}$ min |
|---|---|---|---|---|---|
| | RTMDR$^e$ | K101E$^f$ | E138K$^f$ | | |
| 2 | 3.2 | 47.6 | 34.4 | 0.33 | 55.7 |
| 4 | 4.1 | 14 | 7.5 | 1.21 | 186 |
| 6 | 1.8 | 3.4 | 2.9 | 18.8 | 20.9 |
| 12 | 8.0 | 14 | 10 | 8.28 | 55.7 |
| 26A | 3.46 | 3.89 | 6.93 | 1.77 | 54.7 |
| 28 | 0.74 | 7.63 | 4.11 | 3.26 | 23.0 |
| 34 | 4.88 | 27.3 | 25.7 | 9.11 | 42.0 |

$^e$multi-drug resistant viral strain of HIV-1 RT (provided by US NIH), comprising the amino acid mutation sites of RT enzyme, such as M41L, V106A, T215Y, etc., and resistant to anti-HIV drugs AZT, ddI, and non-nucleoside RT enzyme inhibitor;
$^f$mutated amino acids located at the binding sites of HIV-RT non-nucleoside inhibitors;
$^g$water-solubility and logP value were the values actually measured at pH2.0 (see Edward H.Kerns and Li Di; Drug-like Properties: Concepts, Structure Design and Methods, pages 267, 283);
$^h$incubation experiment of human liver microsomes (see the literature of g, page 335).

Example 45

TZM-bl Cytotoxicity Assay of Compounds

The assay was carried out by reference to the document (Dang, Z, et al. J. Med. Chem. 2009, 52, 7887-7891). In particular, in a 96-well cell culture plate, solutions of Compounds 1-57 at different concentrations (100 µl) were mixed with an equivalent volume of TZM-bl cells (from National Institutes of Health (NIH)) (5×10$^5$/mL), and were incubated at 37° C. for 4 d. 50 µl of freshly prepared XTT solution (1 mg/mL) containing 0.02 µM PMS was added. Optical density at 450 nm was measured 4 h later. CalcuSyn software was used to calculate the 50% cytotoxicity concentration (CC$_{50}$) of the compounds. The results are shown in Table 2.

The experimental results above show that the compounds of formula I according to the invention are new compounds having a strong anti-HIV activity and a good druggability.

Hence, the compounds according to the invention are prospective in developing a novel class of anti-HIV drugs with new structure.

Although the embodiments of the invention have been described in detail, a person skilled in the art would understand that a variety of modifications and replacements may be performed to the details according to all the teachings disclosed therein. These changes all fall into the protection scope of the invention. The scope of the invention is defined by the claims and any equivalent thereof.

The invention claimed is:

1. A compound of formula (I) or pharmaceutically acceptable salt thereof,

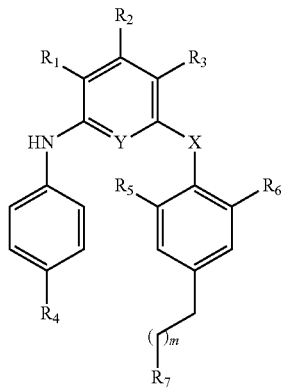

(I)

wherein
$R_1$ is —$NH_2$, —OH, —F, —Cl, —Br, —I, —$NO_2$, —CN, —COOH, —$SO_3H$, —$OCH_3$, —$CH_3$ or —$CF_3$;
$R_2$ is H;
$R_3$ is —$CF_3$, —$CCl_3$, —$CBr_3$, —$COOCH_3$, —$COOCH_2CH_3$, —$COOCH_2CH_2CH_3$, —COOH, —$CONH_2$, —$CONHCH_3$, —$SO_2NH_2$, H, —$NH_2$, —$CONHNH_2$, —OH, —F, —Cl, —Br, —I, —$NO_2$, —CN, —$SO_3H$, —$OCH_3$, —$CH_3$, —$CH_2OH$, —$CH_2Cl$, —$CH_2Br$, —$CH_2NH_2$, —$CH_2OR'$, or —$CH_2NHR'$; wherein R' is

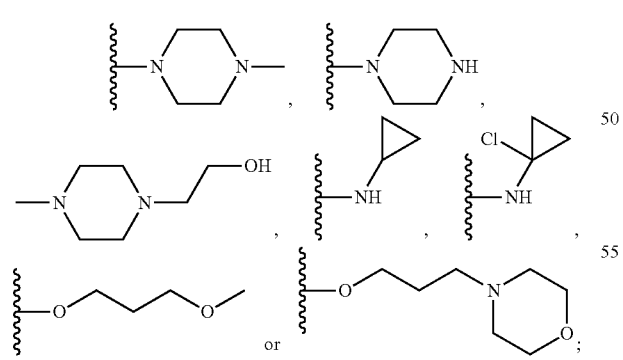

$R_4$ is —CN, —$NH_2$, —OH, —F, —Cl, —Br, —I, —$NO_2$, —COOH, —$SO_3H$, —$OCH_3$, —$CH_3$ or —$CF_3$;
$R_5$ is methyl, ethyl, n-propyl, isopropyl, methoxy, ethoxy, n-propoxy, isopropoxy, fluoro, chloro, bromo, or iodo;
$R_6$ is methyl, ethyl, n-propyl, isopropyl, methoxy, ethoxy, n-propoxy, isopropoxy, fluoro, chloro, bromo, or iodo;
$R_6$ and $R_5$ are identical or different;

$R_7$ is —CN, —$(CH_2)_2$—CN, —$(CH_2)_2$—$CH_3$, —$(CH_2)_2$—$COOCH_3$, —$(CH_2)_3$—OH, —

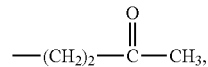

—$(CH_2)_3$—CN, —$(CH_2)_3$—$CH_3$, —$(CH_2)_3$—$COOCH_3$, —$(CH_2)_2$—OH,

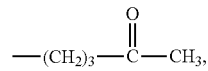

—$(CH_2)_4$—CN, —$(CH_2)_4$—$CH_3$, —$(CH_2)_4$—$COOCH_3$, —$(CH_2)_4$—OH,

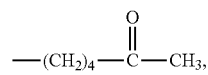

—$CH_2$—CN, —$CH_2$—$CH_3$, —$CH_2$—$COOCH_3$, —$CH_2$—OH,

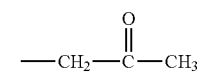

or —$CH_2OR''$; wherein R'' represents $C_{1-6}$ alkyl;
X is —NH— or —O—;
Y is —CH— or —N—, and
m is 0, 1, 2, 3, or 4.

2. The compound or pharmaceutically acceptable salt thereof according to claim 1, wherein
$R_1$ is —$NH_2$;
$R_2$ is H;
$R_3$ is —$CF_3$, —$COOCH_3$, —COOH, —$CONH_2$, —$CONHCH_3$, —$SO_2NH_2$, H, —$NH_2$, —$CONHNH_2$; —OH, —F, —Cl, —Br, —I, —$NO_2$, —CN, —$SO_3H$, —$OCH_3$, —$CH_3$, —$CH_2OH$, —$CH_2OR'$, —$CH_2NH_2$, —$CH_2NHR'$, —$CH_2Cl$ or —$CH_2Br$;
$R_4$ is —CN;
$R_5$ is methyl, methoxy, fluoro, chloro, or bromo;
$R_6$ is methyl, methoxy, fluoro, chloro, or bromo;
$R_6$ and $R_5$ are identical or different;
$R_7$ is —$(CH_2)_2$—CN, —$(CH_2)_2$—$CH_3$, —$(CH_2)_2$—$COOCH_3$, —$(CH_2)_3$—OH or

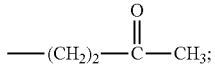

X is —O—; and
Y is —CH— or —N—.

3. A compound or pharmaceutically acceptable salt thereof, wherein the compound is selected from the group consisting of:
5-(4"-cyanoethyl-2",6"-dimethylphenoxy)-$N^1$-(4'-cyanophenyl)-4-trifluoromethyl-1,2-phenylenediamine;
5-(4"-cyanoethyl-2",6"-dimethylphenoxy)-$N^1$-(4'-cyanophenyl)-4-methoxycarbonyl-1,2-phenylenediamine;

5-(4"-cyanoethyl-2",6"-dimethylphenoxy)-N$^1$-(4'-cyanophenyl)-4-hydroxymethyl-1,2-phenylenediamine;

4-carboxyl-5-(4"-cyanoethyl-2",6"-dimethylphenoxy)-N$^1$-(4'-cyanophenyl)-1,2-phenylenediamine;

4-carbamoyl-N$^1$-(4'-cyanophenyl)-5-(4"-cyanoethyl-2",6"-dimethylphenoxy)-1,2-phenylenediamine;

5-(4"-cyanoethyl-2",6"-dimethylphenoxy)-N$^1$-(4'-cyanophenyl)-4-(N-methyl-carbamoyl)-1,2-phenylenediamine;

5-(4"-cyanoethyl-2",6"-dimethylphenoxy)-N$^1$-(4'-cyanophenyl)-4-aminosulfonyl-1,2-phenylenediamine;

N$^2$-(4-cyanoanilinyl)-6-(2,6-dimethyl-4-propylphenoxy)-3-aminopyridine;

N-(4'-cyanophenyl)-5-(4"-hydroxymethyl-2",6"-dimethylphenoxy)-4-hydroxymethyl-2-nitroaniline;

N$^1$-(4'-cyanophenyl)-5-(4"-hydroxymethyl-2",6"-dimethylphenoxy)-4-hydroxymethyl-1,2-phenylenediamine;

N$^2$-(4-cyanoanilinyl)-6-(2,6-difluoro-4-cyanoethyl-phenoxy)-3-aminopyridine;

N$^2$-(4-cyanoanilinyl)-6-(2,6-difluoro-4-methyl propionate phenoxy)-3-aminopyridine;

N$^2$-(4-cyanoanilinyl)-6-(2,6-difluoro-4-(3-hydroxypropyl)phenoxy)-3-aminopyridine;

6-(2-bromo-4-cyanoethyl-5-methoxy)phenoxy-2-(4-cyanoanilinyl)-3-aminopyridine;

6-(2-bromo-4-cyanovinyl-5-methoxy)phenoxy-2-(4-cyanoanilinyl)-3-aminopyridine;

2-(4-cyanoanilinyl)-6-(2,6-dibromo-4-cyanoethyl)phenoxy-3-aminopyridine;

N$^2$-(4-cyanoanilinyl)-6-(2,6-difluoro-4-butanonylphenoxy)-3-aminopyridine;

N$^1$-(4'-cyanophenyl)-5-(4"-cyanovinyl-2",6"-dimethylphenoxy)-4-[(2-methoxyethoxyl)methyl]-1,2-phenylenediamine;

N$^1$-(4'-cyanophenyl)-5-(4"-cyanoethyl-2",6"-dimethylphenoxy)-4-[N-cyclopropylaminomethyl]-1,2-phenylenediamine;

N$^1$-(4'-cyanophenyl)-5-(4"-cyanoethyl-2",6"-dimethylphenoxy)-1,2,4-triaminobenzene;

N$^1$-(4'-cyanophenyl)-5-(4"-cyanoethyl-2",6"-dimethylphenoxy)-4-formhydrazide-1,2-phenylenediamine;

4-acetyloxymethyl-N$^1$-(4'-cyanophenyl)-5-(4"-cyanoethyl-2",6"-dimethylphenoxy)-1,2-phenylenediamine;

N-(4'-cyanophenyl)-5-(4"-cyanoethyl-2",6"-dimethylphenoxy)-4-[methoxymethyl]-1,2-phenylenediamine;

N$^1$-(4'-cyanophenyl)-5-(4"-cyanoethyl-2",6"-dimethylphenoxy)-4-cyclopropionyloxymethyl-1,2-phenylenediamine;

N-(4'-cyanophenyl)-5-(4"-cyanoethyl-2",6"-dimethylphenoxy)-4-[N,N-dimethylaminomethyl]-1,2-phenylenediamine;

N-(4'-cyanophenyl)-5-(4"-cyanoethyl-2",6"-dimethylphenoxy)-4-(N-ethylformamido)-1,2-phenylenediamine;

5-(4"-cyanoethyl-2",6"-dimethylphenoxy)-N$^1$-(4'-cyanophenyl)-4-(N,N-dimethylformamido)-1,2-phenylenediamine; and N-(4'-cyanophenyl)-5-(4"-cyanoethyl-2",6"-dimethylphenoxy)-4-(N-cyclopropylformamido)-1,2-phenylenediamine.

4. A method for preparing the compound or pharmaceutically acceptable salt thereof according to claim 1, the method comprising the scheme as follows:

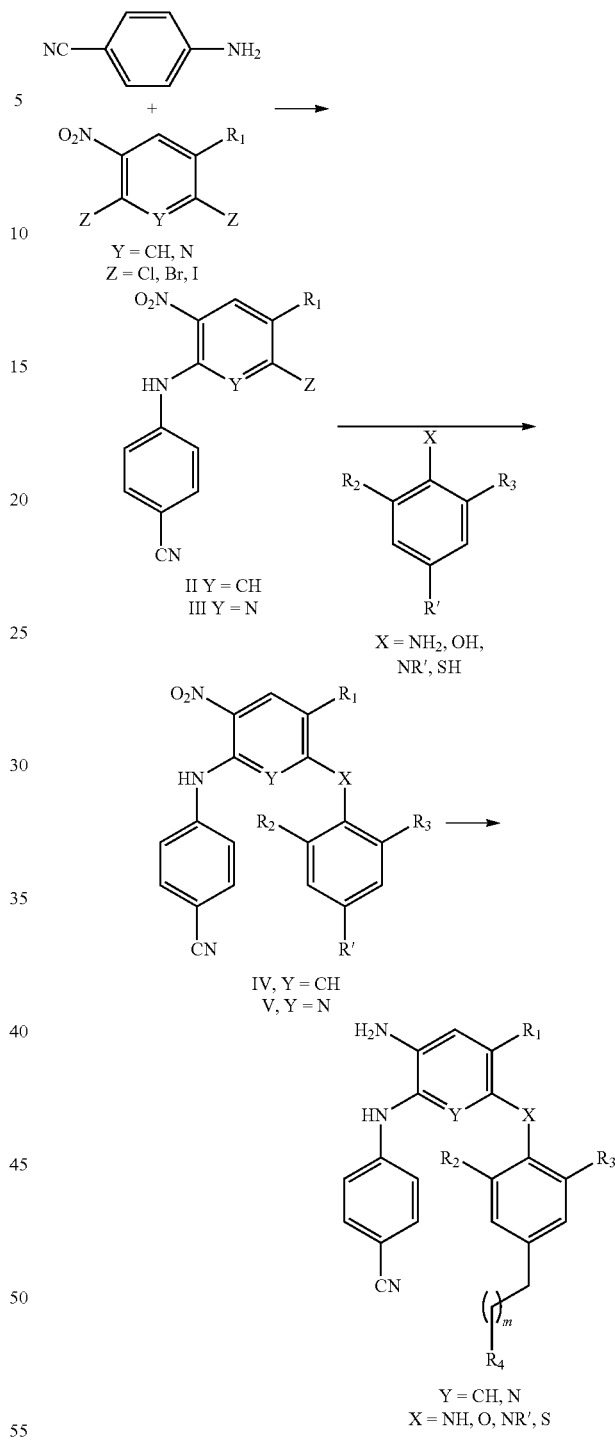

and the method comprising: reacting a substituted 2,6-dihalo benzene or pyridine compound with a p-substituted aniline compound under a basic condition, or using excessive 4-cyano aniline to carry out a solvent-free reaction to produce the intermediate of formula II or III; coupling with a 1,3,5-trisubstituted phenol or aniline compound under a basic condition to get an intermediate (IV or V) having a tricycle backbone structure, then converting the substituent ($R_1$) of the intermediate ring to the corresponding group through conventional functional-group conversion reaction, and finally reducing the nitro group on the intermediate ring to an amino group.

5. A pharmaceutical composition, comprising the compound or pharmaceutically acceptable salt thereof according to claim 1; and, optionally, one or more pharmaceutically acceptable carriers or excipients.

6. A method for treatment and/or assistant treatment of HIV infection or a disease or condition associated with HIV infection, comprising the step of administering an effective amount of the compound or pharmaceutically acceptable salt thereof according to claim 1 to a subject.

7. A method for inhibiting HIV virus in vivo or in vitro, comprising the step of using an effective amount of the compound or pharmaceutically acceptable salt thereof according to claim 1.

8. The method of claim 6, wherein
$R_1$ is —$NH_2$;
$R_2$ is H;
$R_3$ is —$CF_3$, —$COOCH_3$, —COOH, —$CONH_2$, —CONHCH$_3$, —$SO_2NH_2$, H, —$NH_2$, —$CONHNH_2$; —OH, —F, —Cl, —Br, —I, —$NO_2$, —CN, —$SO_3H$, —$OCH_3$, —$CH_3$, —$CH_2OH$, —$CH_2OR'$, —$CH_2NH_2$, —$CH_2NHR'$, —$CH_2Cl$ or —$CH_2Br$;
$R_4$ is —CN;
$R_5$ is methyl, methoxy, fluoro, chloro, or bromo;
$R_6$ is methyl, methoxy, fluoro, chloro, or bromo;
$R_6$ and $R_5$ are identical or different;
$R_7$ is —$(CH_2)_2$—CN, —$(CH_2)_2$—$CH_3$, —$(CH_2)_2$—$COOCH_3$, —$(CH_2)_3$—OH or

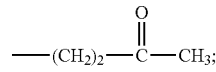

X is —O—; and
Y is —CH— or —N—.

9. The method of claim 6, wherein the compound is selected from the group consisting of:
5-(4"-cyanoethyl-2",6"-dimethylphenoxy)-$N^1$-(4'-cyanophenyl)-4-trifluoromethyl-1,2-phenylenediamine;
5-(4"-cyanoethyl-2",6"-dimethylphenoxy)-$N^1$-(4'-cyanophenyl)-4-methoxycarbonyl-1,2-phenylenediamine;
5-(4"-cyanoethyl-2",6"-dimethylphenoxy)-$N^1$-(4'-cyanophenyl)-4-hydroxymethyl-1,2-phenylenediamine;
4-carboxyl-5-(4"-cyanoethyl-2",6"-dimethylphenoxy)-$N^1$-(4'-cyanophenyl)-1,2-phenylenediamine;
4-carbamoyl-$N^1$-(4'-cyanophenyl)-5-(4"-cyanoethyl-2",6"-dimethylphenoxy)-1,2-phenylenediamine;
5-(4"-cyanoethyl-2",6"-dimethylphenoxy)-$N^1$-(4'-cyanophenyl)-4-(N-methyl-carbamoyl)-1,2-phenylenediamine;
5-(4"-cyanoethyl-2",6"-dimethylphenoxy)-$N^1$-(4'-cyanophenyl)-4-aminosulfonyl-1,2-phenylenediamine;
$N^2$-(4-cyanoanilinyl)-6-(2,6-dimethyl-4-propylphenoxy)-3-aminopyridine;
N-(4'-cyanophenyl)-5-(4"-hydroxymethyl-2",6"-dimethylphenoxy)-4-hydroxymethyl-2-nitroaniline;
N-(4'-cyanophenyl)-5-(4"-hydroxymethyl-2",6"-dimethylphenoxy)-4-hydroxymethyl-1,2-phenylenediamine;
$N^2$-(4-cyanoanilinyl)-6-(2,6-difluoro-4-cyanoethyl-phenoxy)-3-aminopyridine;
$N^2$-(4-cyanoanilinyl)-6-(2,6-difluoro-4-methyl propionate phenoxy)-3-aminopyridine;
$N^2$-(4-cyanoanilinyl)-6-(2,6-difluoro-4-(3-hydroxypropyl)phenoxy)-3-aminopyridine;
6-(2-bromo-4-cyanoethyl-5-methoxy)phenoxy-2-(4-cyanoanilinyl)-3-aminopyridine;
6-(2-bromo-4-cyanovinyl-5-methoxy)phenoxy-2-(4-cyanoanilinyl)-3-aminopyridine;
2-(4-cyanoanilinyl)-6-(2,6-dibromo-4-cyanoethyl)phenoxy-3-aminopyridine;
$N^2$-(4-cyanoanilinyl)-6-(2,6-difluoro-4-butanonylphenoxy)-3-aminopyridine;
$N^1$-(4'-cyanophenyl)-5-(4"-cyanovinyl-2",6"-dimethylphenoxy)-4-[(2-methoxyethoxyl)methyl]-1,2-phenylenediamine;
N-(4'-cyanophenyl)-5-(4"-cyanoethyl-2",6"-dimethylphenoxy)-4-[N-cyclopropylaminomethyl]-1,2-phenylenediamine;
$N^1$-(4'-cyanophenyl)-5-(4"-cyanoethyl-2",6"-dimethylphenoxy)-1,2,4-triaminobenzene;
$N^1$-(4'-cyanophenyl)-5-(4"-cyanoethyl-2",6"-dimethylphenoxy)-4-formhydrazide-1,2-phenylenediamine;
4-acetyloxymethyl-$N^1$-(4'-cyanophenyl)-5-(4"-cyanoethyl-2",6"-dimethylphenoxy)-1,2-phenylenediamine;
N-(4'-cyanophenyl)-5-(4"-cyanoethyl-2",6"-dimethylphenoxy)-4-[methoxymethyl]-1,2-phenylenediamine;
$N^1$-(4'-cyanophenyl)-5-(4"-cyanoethyl-2",6"-dimethylphenoxy)-4-cyclopropionyloxymethyl-1,2-phenylenediamine;
N-(4'-cyanophenyl)-5-(4"-cyanoethyl-2",6"-dimethylphenoxy)-4-[N,N-dimethylaminomethyl]-1,2-phenylenediamine;
N-(4'-cyanophenyl)-5-(4"-cyanoethyl-2",6"-dimethylphenoxy)-4-(N-ethylformamido)-1,2-phenylenediamine;
5-(4"-cyanoethyl-2",6"-dimethylphenoxy)-$N^1$-(4'-cyanophenyl)-4-(N,N-dimethylformamido)-1,2-phenylenediamine; and
N-(4'-cyanophenyl)-5-(4"-cyanoethyl-2",6"-dimethylphenoxy)-4-(N-cyclopropylformamido)-1,2-phenylenediamine.

10. The method of claim 7, wherein
$R_1$ is —$NH_2$;
$R_2$ is H;
$R_3$ is —$CF_3$, —$COOCH_3$, —COOH, —$CONH_2$, —CONHCH$_3$, —$SO_2NH_2$, H, —$NH_2$, —$CONHNH_2$; —OH, —F, —Cl, —Br, —I, —$NO_2$, —CN, —$SO_3H$, —$OCH_3$, $CH_3$, —$CH_2OH$, —$CH_2OR'$, —$CH_2NH_2$, —$CH_2NHR'$, —$CH_2Cl$ or —$CH_2Br$;
$R_4$ is —CN;
$R_5$ is methyl, methoxy, fluoro, chloro, or bromo;
$R_6$ is methyl, methoxy, fluoro, chloro, or bromo;
$R_6$ and $R_5$ are identical or different;
$R_7$ is —$(CH_2)_2$—CN, —$(CH_2)_2$—$CH_3$, —$(CH_2)_2$—$COOCH_3$, —$(CH_2)_3$—OH or

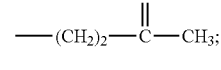

X is —O—; and
Y is —CH— or —N—.

11. The method of claim 7, wherein the compound is selected from the group consisting of:
5-(4"-cyanoethyl-2",6"-dimethylphenoxy)-$N^1$-(4'-cyanophenyl)-4-trifluoromethyl-1,2-phenylenediamine;
5-(4"-cyanoethyl-2",6"-dimethylphenoxy)-$N^1$-(4'-cyanophenyl)-4-methoxycarbonyl-1,2-phenylenediamine;

5-(4"-cyanoethyl-2",6"-dimethylphenoxy)-N¹-(4'-cyanophenyl)-4-hydroxymethyl-1,2-phenylenediamine;
4-carboxyl-5-(4"-cyanoethyl-2",6"-dimethylphenoxy)-N¹-(4'-cyanophenyl)-1,2-phenylenediamine;
4-carbamoyl-N¹-(4'-cyanophenyl)-5-(4"-cyanoethyl-2",6"-dimethylphenoxy)-1,2-phenylenediamine;
5-(4"-cyanoethyl-2",6"-dimethylphenoxy)-N¹-(4'-cyanophenyl)-4-(N-methyl-carbamoyl)-1,2-phenylenediamine;
5-(4"-cyanoethyl-2",6"-dimethylphenoxy)-N¹-(4'-cyanophenyl)-4-aminosulfonyl-1,2-phenylenediamine;
N²-(4-cyanoanilinyl)-6-(2,6-dimethyl-4-propylphenoxy)-3-aminopyridine;
N-(4'-cyanophenyl)-5-(4"-hydroxymethyl-2",6"-dimethylphenoxy)-4-hydroxymethyl-2-nitroaniline;
N-(4'-cyanophenyl)-5-(4"-hydroxymethyl-2",6"-dimethylphenoxy)-4-hydroxymethyl-1,2-phenylenediamine;
N²-(4-cyanoanilinyl)-6-(2,6-difluoro-4-cyanoethyl-phenoxy)-3-aminopyridine;
N²-(4-cyanoanilinyl)-6-(2,6-difluoro-4-methyl propionate phenoxy)-3-aminopyridine;
N²-(4-cyanoanilinyl)-6-(2,6-difluoro-4-(3-hydroxypropyl)phenoxy)-3-aminopyridine;
6-(2-bromo-4-cyanoethyl-5-methoxy)phenoxy-2-(4-cyanoanilinyl)-3-aminopyridine;
6-(2-bromo-4-cyanovinyl-5-methoxy)phenoxy-2-(4-cyanoanilinyl)-3-aminopyridine;
2-(4-cyanoanilinyl)-6-(2,6-dibromo-4-cyanoethyl)phenoxy-3-aminopyridine;
N²-(4-cyanoanilinyl)-6-(2,6-difluoro-4-butanonylphenoxy)-3-aminopyridine;
N¹-(4'-cyanophenyl)-5-(4"-cyanovinyl-2",6"-dimethylphenoxy)-4-[(2-methoxyethoxyl)methyl]-1,2-phenylenediamine;
N-(4'-cyanophenyl)-5-(4"-cyanoethyl-2",6"-dimethylphenoxy)-4-[N-cyclopropylaminomethyl]-1,2-phenylenediamine;
N¹-(4'-cyanophenyl)-5-(4"-cyanoethyl-2",6"-dimethylphenoxy)-1,2,4-triaminobenzene;
N¹-(4'-cyanophenyl)-5-(4"-cyanoethyl-2",6"-dimethylphenoxy)-4-formhydrazide-1,2-phenylenediamine;
4-acetyloxymethyl-N¹-(4'-cyanophenyl)-5-(4"-cyanoethyl-2",6"-dimethylphenoxy)-1,2-phenylenediamine;
N-(4'-cyanophenyl)-5-(4"-cyanoethyl-2",6"-dimethylphenoxy)-4-[methoxymethyl]-1,2-phenylenediamine;
N¹-(4'-cyanophenyl)-5-(4"-cyanoethyl-2",6"-dimethylphenoxy)-4-cyclopropionyloxymethyl-1,2-phenylenediamine;
N-(4'-cyanophenyl)-5-(4"-cyanoethyl-2",6"-dimethylphenoxy)-4-[N,N-dimethylaminomethyl]-1,2-phenylenediamine;
N-(4'-cyanophenyl)-5-(4"-cyanoethyl-2",6"-dimethylphenoxy)-4-(N-ethylformamido)-1,2-phenylenediamine;
5-(4"-cyanoethyl-2",6"-dimethylphenoxy)-N¹-(4'-cyanophenyl)-4-(N,N-dimethylformamido)-1,2-phenylenediamine; and
N-(4'-cyanophenyl)-5-(4"-cyanoethyl-2",6"-dimethylphenoxy)-4-(N-cyclopropylformamido)-1,2-phenylenediamine.

12. The pharmaceutical composition of claim 5, wherein
$R_1$ is —NH₂;
$R_2$ is H;
$R_3$ is —CF₃, —COOCH₃, —COOH, —CONH₂, —CONHCH₃, —SO₂NH₂, H, —NH₂, —CONHNH₂; —OH, —F, —Cl, —Br, —I, —NO₂, —CN, —SO₃H, —OCH₃, —CH₃, —CH₂OH, —CH₂OR', —CH₂NH₂, —CH₂NHR', —CH₂Cl or —CH₂Br;
$R_4$ is —CN;
$R_5$ is methyl, methoxy, fluoro, chloro, or bromo;
$R_6$ is methyl, methoxy, fluoro, chloro, or bromo;
$R_6$ and $R_5$ are identical or different;
$R_7$ is —(CH₂)₂—CN, —(CH₂)₂—CH₃, —(CH₂)₂—COOCH₃, —(CH₂)₃—OH or

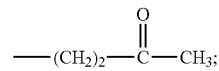

X is —O—; and
Y is —CH— or —N—.

13. The pharmaceutical composition of claim 5, wherein the compound is selected from the group consisting of:
5-(4"-cyanoethyl-2",6"-dimethylphenoxy)-N¹-(4'-cyanophenyl)-4-trifluoromethyl-1,2-phenylenediamine;
5-(4"-cyanoethyl-2",6"-dimethylphenoxy)-N¹-(4'-cyanophenyl)-4-methoxycarbonyl-1,2-phenylenediamine;
5-(4"-cyanoethyl-2",6"-dimethylphenoxy)-N¹-(4'-cyanophenyl)-4-hydroxymethyl-1,2-phenylenediamine;
4-carboxyl-5-(4"-cyanoethyl-2",6"-dimethylphenoxy)-N¹-(4'-cyanophenyl)-1,2-phenylenediamine;
4-carbamoyl-N¹-(4'-cyanophenyl)-5-(4"-cyanoethyl-2",6"-dimethylphenoxy)-1,2-phenylenediamine;
5-(4"-cyanoethyl-2",6"-dimethylphenoxy)-N¹-(4'-cyanophenyl)-4-(N-methyl-carbamoyl)-1,2-phenylenediamine;
5-(4"-cyanoethyl-2",6"-dimethylphenoxy)-N¹-(4'-cyanophenyl)-4-aminosulfonyl-1,2-phenylenediamine;
N²-(4-cyanoanilinyl)-6-(2,6-dimethyl-4-propylphenoxy)-3-aminopyridine;
N-(4'-cyanophenyl)-5-(4"-hydroxymethyl-2",6"-dimethylphenoxy)-4-hydroxymethyl-2-nitroaniline;
N-(4'-cyanophenyl)-5-(4"-hydroxymethyl-2",6"-dimethylphenoxy)-4-hydroxymethyl-1,2-phenylenediamine;
N²-(4-cyanoanilinyl)-6-(2,6-difluoro-4-cyanoethyl-phenoxy)-3-aminopyridine;
N²-(4-cyanoanilinyl)-6-(2,6-difluoro-4-methyl propionate phenoxy)-3-aminopyridine;
N²-(4-cyanoanilinyl)-6-(2,6-difluoro-4-(3-hydroxypropyl)phenoxy)-3-aminopyridine;
6-(2-bromo-4-cyanoethyl-5-methoxy)phenoxy-2-(4-cyanoanilinyl)-3-aminopyridine;
6-(2-bromo-4-cyanovinyl-5-methoxy)phenoxy-2-(4-cyanoanilinyl)-3-aminopyridine;
2-(4-cyanoanilinyl)-6-(2,6-dibromo-4-cyanoethyl)phenoxy-3-aminopyridine;
N²-(4-cyanoanilinyl)-6-(2,6-difluoro-4-butanonylphenoxy)-3-aminopyridine;
N¹-(4'-cyanophenyl)-5-(4"-cyanovinyl-2",6"-dimethylphenoxy)-4-[(2-methoxyethoxyl)methyl]-1,2-phenylenediamine;
N-(4'-cyanophenyl)-5-(4"-cyanoethyl-2",6"-dimethylphenoxy)-4-[N-cyclopropylaminomethyl]-1,2-phenylenediamine;
N¹-(4'-cyanophenyl)-5-(4"-cyanoethyl-2",6"-dimethylphenoxy)-1,2,4-triaminobenzene;
N¹-(4'-cyanophenyl)-5-(4"-cyanoethyl-2",6"-dimethylphenoxy)-4-formhydrazide-1,2-phenylenediamine;
4-acetyloxymethyl-N¹-(4'-cyanophenyl)-5-(4"-cyanoethyl-2",6"-dimethylphenoxy)-1,2-phenylenediamine;
N-(4'-cyanophenyl)-5-(4"-cyanoethyl-2",6"-dimethylphenoxy)-4-[methoxymethyl]-1,2-phenylenediamine;

$N^1$-(4'-cyanophenyl)-5-(4"-cyanoethyl-2",6"-dimethylphenoxy)-4-cyclopropionyloxymethyl-1,2-phenylenediamine;

N-(4'-cyanophenyl)-5-(4"-cyanoethyl-2",6"-dimethylphenoxy)-4-[N,N-dimethylaminomethyl]-1,2-phenylenediamine;

N-(4'-cyanophenyl)-5-(4"-cyanoethyl-2",6"-dimethylphenoxy)-4-(N-ethylformamido)-1,2-phenylenediamine;

5-(4"-cyanoethyl-2",6"-dimethylphenoxy)-$N^1$-(4'-cyanophenyl)-4-(N,N-dimethylformamido)-1,2-phenylenediamine; and N-(4'-cyanophenyl)-5-(4"-cyanoethyl-2",6"-dimethylphenoxy)-4-(N-cyclopropylformamido)-1,2-phenylenediamine.

* * * * *